United States Patent
Pathy

(10) Patent No.: US 10,816,147 B2
(45) Date of Patent: Oct. 27, 2020

(54) LIGHTING DEVICE WITH CAVITY FOR REMOVABLY ATTACHING TO A TOOL

(71) Applicant: Pathy Medical, LLC, Shelton, CT (US)

(72) Inventor: Vinod V. Pathy, Madison, CT (US)

(73) Assignee: PATHY MEDICAL, LLC, Shelton, CT (US)

( * ) Notice: Subject to any disclaimer, the term of this patent is extended or adjusted under 35 U.S.C. 154(b) by 20 days.

(21) Appl. No.: 15/849,827

(22) Filed: Dec. 21, 2017

(65) Prior Publication Data

US 2018/0135814 A1    May 17, 2018

Related U.S. Application Data

(63) Continuation of application No. 14/242,819, filed on Apr. 1, 2014, now Pat. No. 9,851,060.
(Continued)

(51) Int. Cl.
*F21L 4/02* (2006.01)
*F21V 33/00* (2006.01)
(Continued)

(52) U.S. Cl.
CPC .............. *F21L 4/02* (2013.01); *A61B 90/30* (2016.02); *F21V 33/0068* (2013.01);
(Continued)

(58) Field of Classification Search
CPC .. F21V 33/0068; F21V 33/0084; F21V 21/08; F21V 21/0885; F21V 21/0965; A61B 19/06; A61B 19/0607; A61B 19/5202; A61B 19/521; A61B 2019/521; A61B 1/0669; A61B 1/0676; A61B 1/0684; B25B 23/18
See application file for complete search history.

(56) References Cited

U.S. PATENT DOCUMENTS 2,242,536 A    5/1941   Montgomery
4,539,003 A    9/1985   Tucker
(Continued)

FOREIGN PATENT DOCUMENTS

CN    200982612 Y    11/2007
DE    202004002963 U1    4/2004
(Continued)

OTHER PUBLICATIONS

MarineBuzz.com, "Use LED Clever Collar to Light up Your Work Space," website printout from https://web.archive.org/web/20080918055357/http://www.marinebuzz.com/2008/09/14/use-led-clever-collar-to-light-up-your-work-space/, Sep. 14, 2008, 1 page.

*Primary Examiner* — Isiaka O Akanbi
*Assistant Examiner* — Steven Y Horikoshi
(74) *Attorney, Agent, or Firm* — McCarter & English, LLP

(57) ABSTRACT

A cordless light attachment for a tool includes a housing that has a proximal end and a distal end, and an interior cavity that extends from the proximal end to the distal end, forming an opening extending through the housing from the proximal end to the distal end. The device receives therein a tool and removably attaches to the tool. The device has at least one light source powered by a cordless power source arranged on or within the housing.

23 Claims, 19 Drawing Sheets

Related U.S. Application Data

(60) Provisional application No. 61/853,232, filed on Apr. 1, 2013.

(51) Int. Cl.
    *A61B 90/30*     (2016.01)
    *A61B 18/14*     (2006.01)

(52) U.S. Cl.
    CPC ...... *F21V 33/0084* (2013.01); *A61B 18/1402* (2013.01); *A61B 2090/309* (2016.02)

(56) References Cited

U.S. PATENT DOCUMENTS

| | | |
|---|---|---|
| 4,542,741 A | 9/1985 | Burgin |
| 4,619,248 A | 10/1986 | Walsh |
| 4,657,012 A | 4/1987 | Burgin |
| 5,281,134 A | 1/1994 | Schultz |
| 5,683,246 A | 11/1997 | Coss et al. |
| 5,692,863 A | 12/1997 | Louw |
| 5,716,320 A | 2/1998 | Buttermore |
| 5,785,408 A | 7/1998 | Tseng |
| 5,845,986 A * | 12/1998 | Breen ............... B25B 23/18 362/119 |
| 5,908,433 A | 6/1999 | Eager et al. |
| 5,928,140 A | 7/1999 | Hardten |
| 5,967,971 A | 10/1999 | Bolser |
| 6,080,105 A | 6/2000 | Spears |
| 6,084,422 A | 7/2000 | Bartholomew |
| 6,095,810 A | 8/2000 | Bianchetti |
| 6,129,662 A | 10/2000 | Li et al. |
| 6,142,995 A | 11/2000 | Cosmescu |
| 6,196,968 B1 | 3/2001 | Rydin et al. |
| 6,213,621 B1 | 4/2001 | Chien |
| 6,223,633 B1 | 5/2001 | Chien-Chich |
| 6,228,025 B1 | 5/2001 | Hipps et al. |
| 6,277,064 B1 | 8/2001 | Yoon |
| 6,322,499 B1 | 11/2001 | Evans et al. |
| 6,325,522 B1 | 12/2001 | Walian |
| 6,358,244 B1 | 3/2002 | Newman et al. |
| 6,379,065 B2 | 4/2002 | Perry et al. |
| 6,394,950 B1 | 5/2002 | Weiss |
| 6,409,705 B1 | 6/2002 | Kondo |
| 6,428,180 B1 * | 8/2002 | Karram ............... A61B 5/0059 362/109 |
| 6,496,718 B1 | 12/2002 | Lonky |
| 6,497,654 B1 | 12/2002 | Leonard et al. |
| 6,504,985 B2 | 1/2003 | Parker et al. |
| 6,517,551 B1 | 2/2003 | Driskill |
| 6,540,390 B2 | 4/2003 | Toth et al. |
| 6,554,768 B1 | 4/2003 | Leonard |
| 6,562,032 B1 | 5/2003 | Ellman et al. |
| 6,585,727 B1 | 7/2003 | Cashman et al. |
| 6,602,188 B2 | 8/2003 | Bolser |
| 6,648,902 B2 | 11/2003 | Colgan et al. |
| 6,739,744 B2 | 5/2004 | Williams et al. |
| 6,769,911 B2 | 8/2004 | Buchalla et al. |
| 6,805,666 B2 | 10/2004 | Holland et al. |
| 6,817,978 B2 | 11/2004 | Holland et al. |
| 6,955,444 B2 | 10/2005 | Gupta |
| 6,971,989 B2 | 12/2005 | Yossepowitch |
| 6,988,814 B1 * | 1/2006 | Correa ............... A61B 17/30 362/109 |
| 7,008,076 B2 | 3/2006 | Zirk |
| 7,063,436 B2 | 6/2006 | Steen et al. |
| 7,083,613 B2 | 8/2006 | Treat |
| 7,106,523 B2 | 9/2006 | McLean et al. |
| 7,108,395 B2 | 9/2006 | Correa |
| 7,112,199 B2 | 9/2006 | Cosmescu |
| 7,141,015 B2 | 11/2006 | Ruane |
| 7,270,439 B2 | 9/2007 | Horrell et al. |
| 7,309,341 B2 | 12/2007 | Ortiz et al. |
| 7,322,135 B2 | 1/2008 | Gulati |
| 7,390,298 B2 | 6/2008 | Chu |
| 7,393,114 B2 | 7/2008 | Devlin |
| 7,399,101 B2 | 7/2008 | Clausen et al. |
| 7,481,766 B2 | 1/2009 | Lee et al. |
| 7,500,947 B2 | 3/2009 | Kucklick |
| 7,503,894 B2 | 3/2009 | Vankoski et al. |
| 7,534,104 B2 | 5/2009 | Schneider |
| 7,631,981 B2 | 12/2009 | Miller et al. |
| 7,748,979 B2 | 7/2010 | Nahlieli |
| 7,832,914 B2 | 11/2010 | Liu |
| 7,922,378 B2 | 4/2011 | Bausenwein et al. |
| 7,927,240 B2 | 4/2011 | Lynch |
| 7,954,687 B2 | 6/2011 | Zemlok et al. |
| 7,976,559 B2 | 7/2011 | Goldfarb et al. |
| 8,038,439 B2 | 10/2011 | Schatz et al. |
| 8,047,987 B2 | 11/2011 | Grey et al. |
| 8,075,553 B2 | 12/2011 | Scheller et al. |
| 8,131,380 B2 | 3/2012 | Cao et al. |
| 8,132,949 B2 | 3/2012 | Vayser et al. |
| 8,152,718 B2 | 4/2012 | Cheng |
| 8,162,852 B2 | 4/2012 | Norris |
| 8,172,834 B2 | 5/2012 | Bhadri et al. |
| 8,186,864 B2 | 5/2012 | Komazaki et al. |
| 8,246,230 B2 | 8/2012 | Todd et al. |
| 8,267,855 B2 | 9/2012 | Barker |
| 8,328,402 B2 | 12/2012 | O'Leary et al. |
| 8,371,848 B2 | 2/2013 | Okawa et al. |
| 8,377,049 B2 | 2/2013 | Cho et al. |
| 8,403,843 B2 | 3/2013 | Bruto Da Costa |
| 8,419,428 B2 | 4/2013 | Lawrence |
| 8,469,707 B2 | 6/2013 | Emde |
| 8,485,972 B2 | 7/2013 | Papac et al. |
| 8,496,475 B2 | 7/2013 | Jamnia |
| 8,506,565 B2 | 8/2013 | DeCarlo |
| 8,556,485 B2 | 10/2013 | Geuder et al. |
| 8,636,658 B2 | 1/2014 | Su et al. |
| 8,684,577 B2 | 4/2014 | Vayser |
| 8,690,872 B2 | 4/2014 | Jayaraj |
| 8,721,539 B2 | 5/2014 | Shohat et al. |
| 8,758,224 B2 | 6/2014 | Viola |
| 8,876,709 B2 | 11/2014 | Vayser et al. |
| 8,876,713 B2 | 11/2014 | Subramaniam |
| 8,882,756 B2 | 11/2014 | Greeley et al. |
| 8,968,347 B2 | 3/2015 | McCollam |
| 9,005,115 B2 | 4/2015 | Vayser |
| 9,011,323 B2 | 4/2015 | Vayser et al. |
| 9,023,039 B2 | 5/2015 | Kerr |
| 9,050,048 B2 | 6/2015 | Nadershahi et al. |
| 9,055,935 B2 | 6/2015 | Grey et al. |
| 9,060,707 B2 | 6/2015 | Grey et al. |
| 9,072,452 B2 | 7/2015 | Vayser et al. |
| 9,107,650 B2 | 8/2015 | Bjork et al. |
| 9,125,587 B2 | 9/2015 | Hawkins et al. |
| 2004/0166475 A1 | 8/2004 | Nikolov |
| 2004/0242970 A1 | 12/2004 | Burns |
| 2005/0065496 A1 | 3/2005 | Simon et al. |
| 2005/0231945 A1 | 10/2005 | Leibinger et al. |
| 2006/0189849 A1 | 8/2006 | Sharratt et al. |
| 2006/0282072 A1 | 12/2006 | DesRosier |
| 2007/0049927 A1 | 3/2007 | Saltzman |
| 2007/0060795 A1 | 3/2007 | Vayser et al. |
| 2007/0066872 A1 | 3/2007 | Morrison et al. |
| 2007/0093693 A1 | 4/2007 | Geist et al. |
| 2007/0110496 A1 | 5/2007 | Cetera |
| 2008/0147058 A1 | 6/2008 | Horrell et al. |
| 2008/0266840 A1 | 10/2008 | Nordmeyer et al. |
| 2008/0266845 A1 | 10/2008 | Wu et al. |
| 2008/0275435 A1 | 11/2008 | Nadolski |
| 2009/0054169 A1 | 2/2009 | DeCarlo |
| 2009/0198108 A1 | 8/2009 | Chen et al. |
| 2010/0030033 A1 | 2/2010 | Farley et al. |
| 2010/0106015 A1 | 4/2010 | Norris |
| 2010/0118555 A1 | 5/2010 | Lee |
| 2010/0125172 A1 | 5/2010 | Jayaraj |
| 2010/0190129 A1 | 7/2010 | Paz |
| 2010/0274097 A1 | 10/2010 | Cho et al. |
| 2010/0312241 A1 | 12/2010 | Erickson, Jr. |
| 2011/0060332 A1 | 3/2011 | Cheng |
| 2011/0143304 A1 | 6/2011 | Jamnia et al. |
| 2011/0190768 A1 | 8/2011 | Shvetsov et al. |
| 2011/0216533 A1 | 9/2011 | Bertken |

(56) References Cited

U.S. PATENT DOCUMENTS

| | | |
|---|---|---|
| 2011/0257488 A1 | 10/2011 | Koyama et al. |
| 2011/0261583 A1 | 10/2011 | Geuder et al. |
| 2011/0279056 A1 | 11/2011 | Waelti et al. |
| 2011/0289780 A1 | 12/2011 | Tiegs |
| 2011/0301421 A1 | 12/2011 | Michaeli et al. |
| 2012/0059226 A1 | 3/2012 | Funt |
| 2012/0149992 A1 | 6/2012 | Duggal et al. |
| 2012/0219923 A1 | 8/2012 | Kert |
| 2012/0221000 A1 | 8/2012 | Bromley et al. |
| 2012/0283718 A1 | 11/2012 | Cosmesceu |
| 2012/0283728 A1 | 11/2012 | Cosmescu |
| 2013/0041227 A1 | 2/2013 | Chan et al. |
| 2013/0197317 A1 | 8/2013 | Daniel et al. |
| 2013/0267787 A1 | 10/2013 | Warnock |
| 2013/0331657 A1 | 12/2013 | Basson |
| 2014/0081086 A1 | 3/2014 | Shvetsov et al. |
| 2015/0025324 A1 | 1/2015 | Wan |
| 2015/0238088 A1 | 8/2015 | Hufnagel et al. |

FOREIGN PATENT DOCUMENTS

| | | |
|---|---|---|
| JP | H07275261 A | 10/1995 |
| JP | 2000316874 A | 11/2000 |
| JP | 2005193012 A | 7/2005 |
| JP | 2005312727 A | 11/2005 |
| JP | 2009153785 A | 7/2009 |
| JP | 2012034804 A | 2/2012 |
| JP | 3174490 U | 3/2012 |
| RU | 2355562 C1 | 5/2009 |
| WO | 2006065271 A2 | 6/2006 |
| WO | 2013036625 A1 | 3/2013 |

* cited by examiner

LIGHTING DEVICE WITH CAVITY FOR REMOVABLY ATTACHING TO A TOOL

CROSS-REFERENCE TO RELATED APPLICATIONS

The patent application is a continuation of co-pending U.S. application Ser. No. 14/242,819, which is entitled "Lighting Device for Attachment to a Tool" and was filed Apr. 1, 2014, and claims benefit under 35 U.S.C. § 119(e) to U.S. provisional application Ser. No. 61/853,232, filed Apr. 1, 2013, titled "Operative Instrument Light Attachment," all of which are hereby expressly incorporated by reference as part of the present disclosure.

FIELD OF THE INVENTION

The present invention relates to a lighting device. More particularly, the invention relates to a wireless lighting device that is attachable to a tool or object.

BACKGROUND OF THE INVENTION

A lighting device is used to allow an operator to illuminate, and thus more precisely control and enhance, a space or area with a lighted field of view. In many situations, a lighting device can be used to illuminate a closed or confined space that would not regularly receive an adequate amount of light, if at all. Existing lighting devices are connectable to a variety of tools, including, for example, medical devices and screwdrivers, to illuminate the area in which the device or tool is to be used. Such lighting devices and light sources include attachments that have an electrical cord extending therefrom that in turn is connectable to a power source, attachments that are battery powered, and light sources integrally formed within a tool to direct light on a specific field of view.

In medical practice, lighting devices are used to direct light at a specific area being operated on or examined. For example, lighting devices can be used in conjunction with electrosurgical handheld devices, such as a BOVIE® pen used to incise through tissues, and a variety of other operative instruments, such as retractors and forceps. Lighted retractors are commonly used during surgeries to help illuminate the surgical field.

The inventor has discerned a number of disadvantages of previously known lighting devices. For example, known lighting devices that include a light source integrally formed therein are generally expensive, bulky, and can cause injury. Known cordless and corded lighting devices add significant bulk to a tool preventing a user from manipulating the tool with the precision required in many situations and being able to extend the tool into tight spaces. Additionally, many lighting device, especially corded lighting devices, require constant repositioning, are cumbersome, are assistant-dependent to hold or re-position, and can be disruptive to a surgical field. Further, corded lighting devices as well as light sources integrally formed within a tool can become hot, burn the user and/or the patient, and possibly even cause a fire. Headlights can be used as an alternative to a lighting device. However, similar to lighting devices, headlights are bulky, commonly require cables to connect to a power source, require constant readjustment, and can pose a potential safety hazard. Moreover, being worn on the head, they are at a distance from the surgical field, decreasing their effectiveness, and can be cumbersome to the user, and cause fatigue if worn for an extended period of time.

SUMMARY OF THE INVENTION

Accordingly, it is an object of the present invention to overcome one or more of the above-described drawbacks and/or disadvantages of the prior art.

The present invention relates to a cordless lighting device that is attachable to a tool or object to illuminate a field of view. In configurations where the device slides onto and over the end of a tool, it provides a minimized profile as compared to previously known devices and a more symmetric field of illumination. The device is securely retained on the tool during use but can be removed. The lighting device in certain embodiments can be automatically activated upon attachment to the tool or object and deactivated upon disengagement from the tool or device.

In certain embodiments, the lighting device has a housing having a proximal end and a distal end with a substantially tapered or conical interior cavity extending from the proximal end to the distal end and forming an opening extending through the housing from the proximal end to the distal end. One or more lights at the distal end of the housing illuminate a field of view. An on-board power source in the device, such as, for example, a battery, powers the light(s). The device removably attaches to a tapered or conical portion of a tool. The cavity is shaped and configured so that it receives and attaches to a certain portion of the tool. In such manner, the location of the lighting device can be selected where most advantageous. For example, in the case of a surgical tool, the device can be located close to the cutting portion of the tool, so that it is as close as possible to the surgical site and provides as good, e.g., direct, illumination as possible.

In certain embodiments, the lighting device includes a housing that has a proximal end and a distal end and an interior cavity that forms an opening extending through the housing from the proximal end to the distal end. One or more lights at the distal end of the housing illuminate a field of view. An on-board power source in the device, such as, for example, a battery, powers the light(s). The device removably attaches to the tool by one or more self-locking protrusions that extend at a forward angle (toward the distal end) into the cavity. Upon installation of the device on the tool, e.g., in a direction from distal end of the tool toward the proximal end of the tool, the protrusion(s) may flex forward and/or upward to allow relative sliding motion between the device and the tool. However, upon attempted movement of the device in the direction of the distal end of the tool, due to the forward angle of the protrusion(s), the protrusion(s) will be pulled by engagement with the tool into a proximal and/or downward direction. This will create a wedging effect and/or increase the force of the protrusion(s) against the surface of the tool, increasing the force holding the device on the tool. This mitigates the chances of the device unintentionally detaching from the tool.

In some embodiments, the lighting device has a split collar portion at the distal and/or proximal end. The slit on the collar permits the lighting device to expand to accommodate the tool in the cavity. In such manner, the device can be installed upon different size tools. The spring force in the material of the split collar applies compression force on the shaft to help secure the device to the tool, e.g., frictionally.

Some tools have multiple inter-fitting pieces in which a first part, such as a blade, are insertably attachable into a second part of the tool, such as a handle. In some embodiments of the lighted device, the second part of the tool or handle is received within the cavity of the device, and the first tool part, e.g., blade, can be inserted and secured into the second part. In some such tools, the first part has a collar extending radially outwardly that in normal use abuts against the end of the tool. In some embodiments of the lighted device, the distal end has a contact portion or flange having an inner diameter that is smaller than the outer diameter of the blade collar. Upon insertion/securing of the tool first part into the second part, the collar contacts or abuts against the contact portion of the device, securing the device to the tool and helping to prevent the device from unintentionally disengaging from the tool.

In certain embodiments, the lighting device automatically illuminates when installed on the tool and/or de-illuminates upon removal from the tool. For example, some embodiments have a first plate within the housing toward a distal end having electronic components affixed thereon in electrical communication with the lights, and a second plate within the housing toward a proximal end of the housing with electronic components thereon. The first plate, second plate, and power source can form a complete electrical circuit delivering power to the lights, and thus creating illumination. In the uninstalled position, the electrical circuit with the power source, e.g., a battery is not complete and the lights are not illuminated. When the device is installed on the tool, the electrical circuit is completed and illuminates the lights. When the device is uninstalled from the tool, the circuit is again opened and the lights de-illuminated.

One advantage of the invention is that the lighting device is more compact than previous devices. Another advantage is that the lighting device is easily attachable to a tool and detachable from the tool. Yet another advantage is that the lighting device can simultaneously attach to a tool and illuminates a light source ensuring efficient and easy assembly and use. A further advantage is that the lighting device is securable to the tool at or over a desired portion of the tool. These and other objects and advantages of the present invention, and/or of the currently preferred embodiments thereof, will become more readily apparent in view of the following detailed description and accompanying drawings.

DETAILED DESCRIPTION OF EMBODIMENTS OF THE INVENTION

The present invention now will be described more fully hereinafter with reference to the accompanying drawings, in which embodiments of the invention are shown. The invention may, however, be embodied in many different forms and should not be construed as limited to the embodiments set forth herein. Like numbers refer to like elements throughout.

Figure 1:
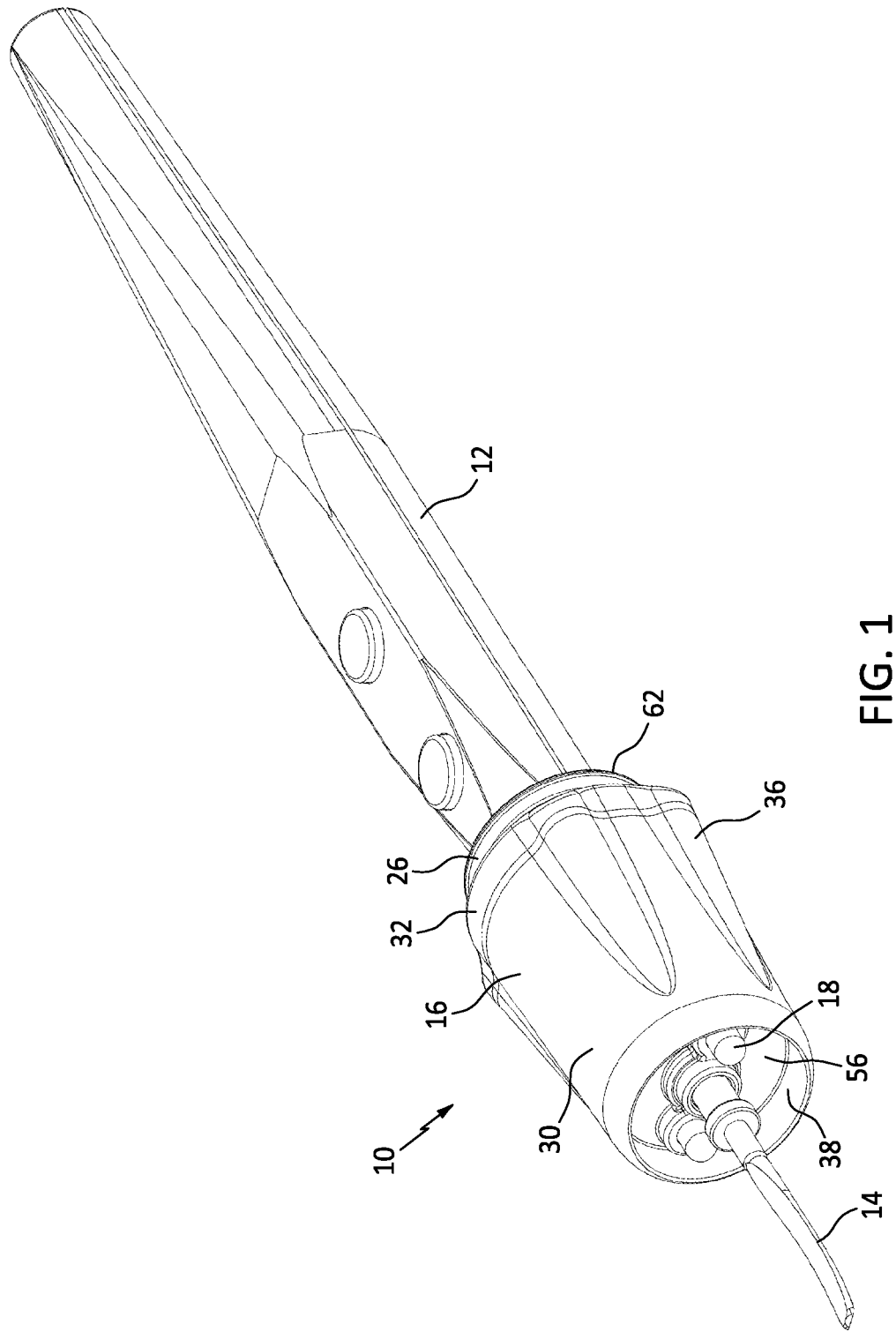
FIG. 1 is the front perspective view of a lighting device positioned on a tool with a shaft of the tool extending through the lighting device.
Figure 2:
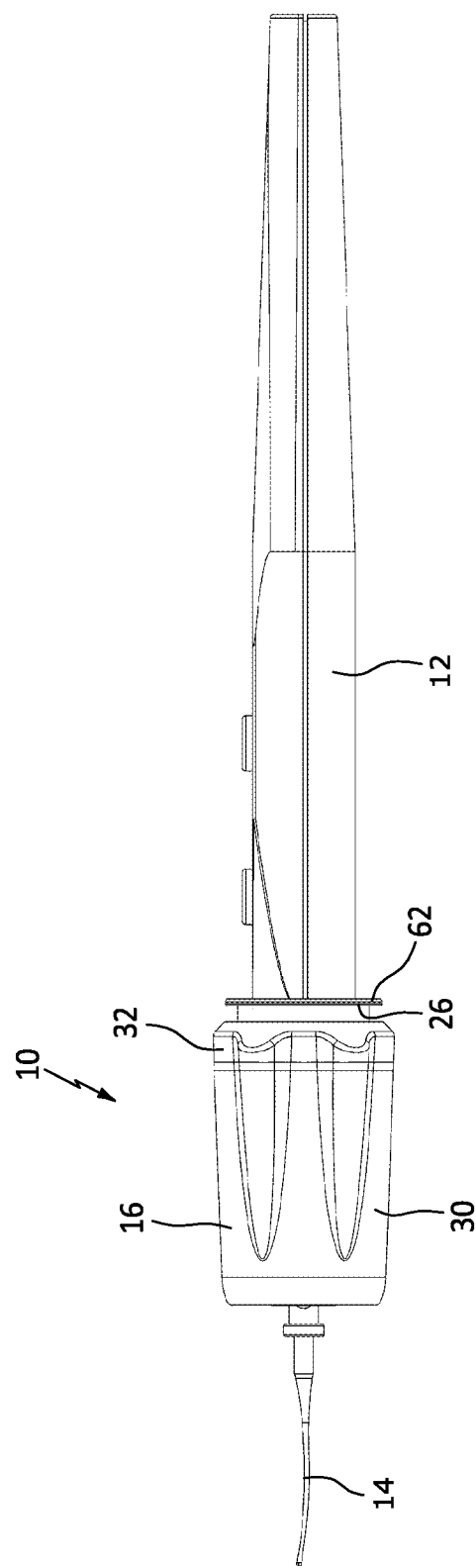
FIG. 2 is a right side view of the lighting device of FIG. 1 connected to the tool.
Figure 3:
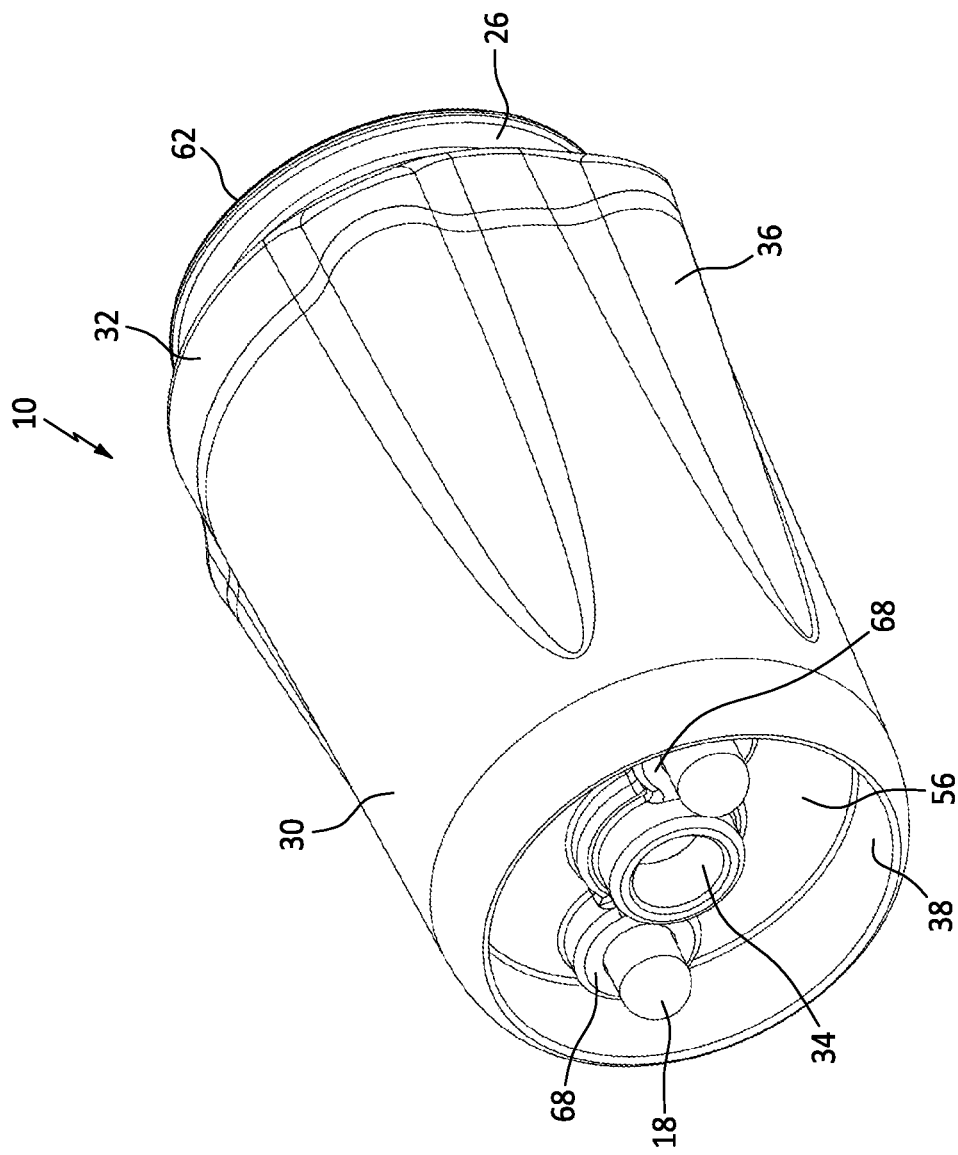
FIG. 3 is a front perspective view of the lighting device of FIG. 1.
Figure 4:
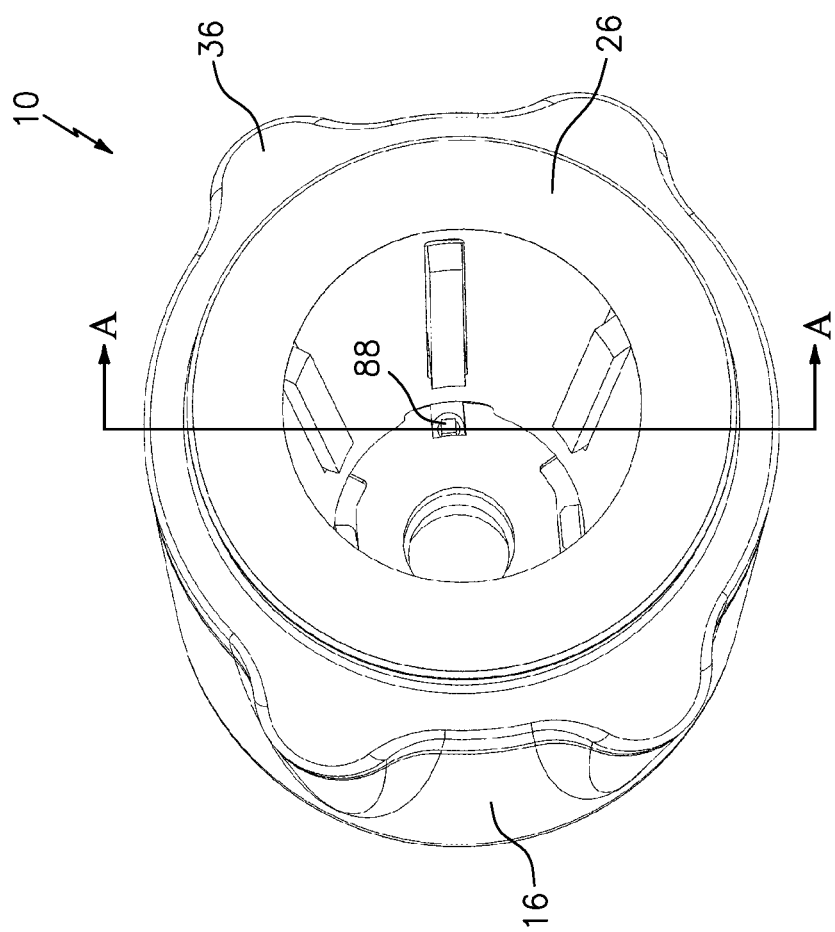
FIG. 4 is a rear perspective view of the lighting device of FIG. 1.
Figure 5:
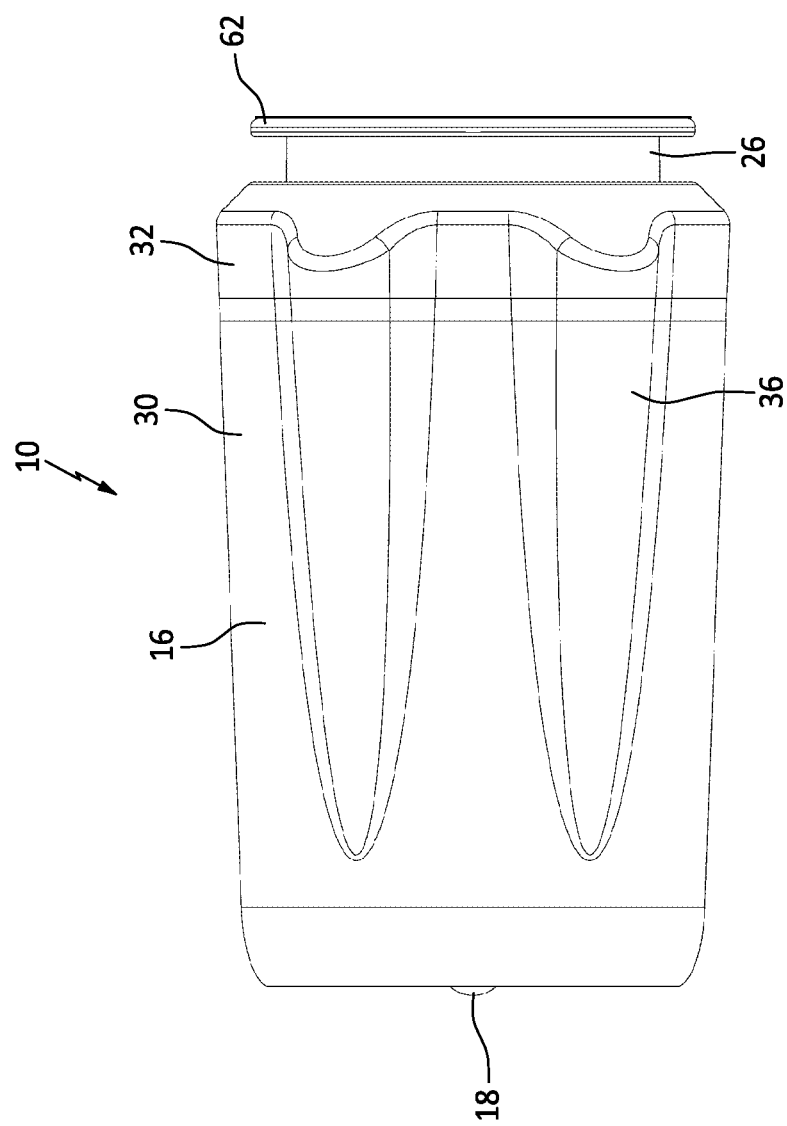
FIG. 5 is right side view of the lighting device of FIG. 1.
Figure 6:
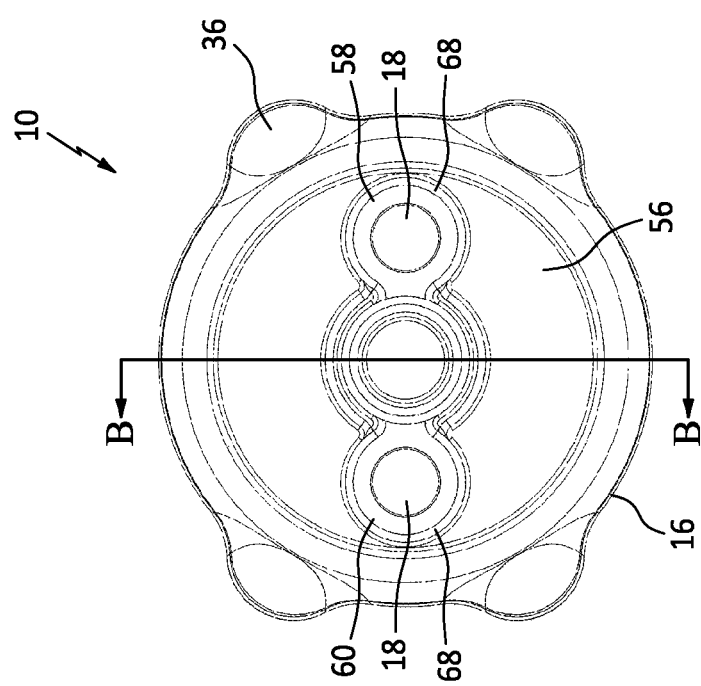
FIG. 6 is a front view of the lighting device of FIG. 1.
Figure 7:
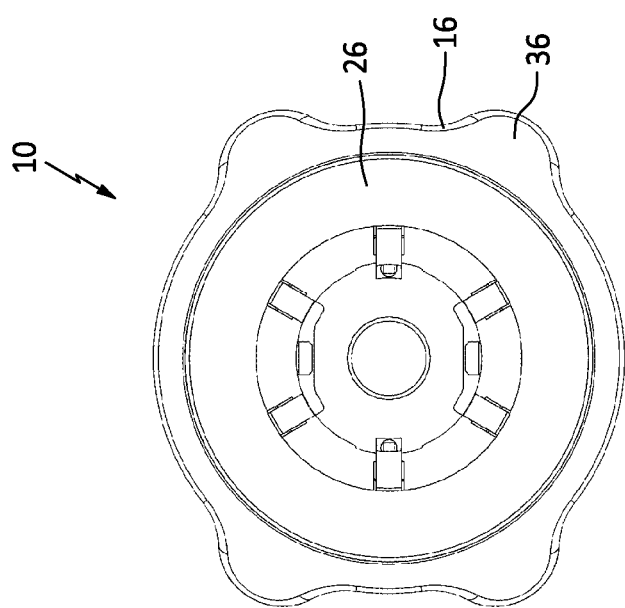
FIG. 7 is rear view of the lighting device of FIG. 1.

As shown in an embodiment in FIGS. 1 and 2, a cordless lighting device, indicated generally by the reference numeral 10, is installed onto and over a portion of a distal end of the tool 12 and is removably thereto. A shaft 14 of the tool 12 can subsequently extend through an opening extending from a proximal end to a distal end of the lighting device 10 so that the device 10 surrounds the tool 12. In the illustrated embodiment, the tool 12 is a BOVIE® pen, and the shaft 14 the blade of the BOVIE® pen. However, the present invention may be installed upon various different types of tools, both surgical and non-surgical, of various shapes and dimensions. As should be understood by those of ordinary skill in the art in accord with the detailed description herein, the dimension and shape of the light device 10 and its various features can be altered to accommodate and install on the desired tool.

In general, once the lighting device 10 is frictionally engaged to a predetermined position on a tool 12, a directed stream of light automatically projects from the device 10. The lighting device 10 can be turned off and disengaged from the tool 12 by applying an axial force at the proximal end of the light attachment 10, which in turn disengages the lighting device 10 from the tool 12. In an embodiment, the lighting device can alternatively include an on/off switch or button to control the operability of the light source.

FIGS. 3-7 illustrate various views and features of the lighting device 10. As will be described in more detail below, the lighting device 10 generally includes a housing 16, at least one light source 18, a first plate 20, a frame 22, a second plate 24, a sleeve 26 and a power source 28.

As shown in FIGS. 3-7 and 10, the housing 16 includes a first housing element 30 and a second housing element 32 that is receivable within the first housing element 30 or otherwise connectable with the first housing element 30 to form the housing 16. In some embodiments, the first housing element 30 and a second housing element 32 form a substantially fluid tight seal when connected so as to protect the internal components from fluid incursion into the housing 16. Although the housing 18 includes two housing elements 30, 32 in the embodiment shown, the housing 18 can readily be made of a single unitary element in place of the two independent elements.

The first housing element 30 includes an opening 34 extending from a proximal end to a distal end so as to define an internal cavity, a plurality of projections 36 that project outwardly about an outer periphery of the first housing element 30, and a recess 38 extending inwardly at a distal end of the housing 16 toward the proximal end. The light source 18 is located in the recess 38. Thus, the recess 38 protects the light source 18 from contact with external surfaces. Conversely, the recess 38 helps limit or prevent the light source 18 from contacting external surfaces, such as tissue, that might be damaged by direct contact with the light source 18. The recess 38 also aids in directing the light source 18 toward a particular space being illuminated. In some embodiments, surfaces of the recess 38 can be made of or coated with a reflective material, and in combination with the shape of the recess, as those of ordinary skill in the art should appreciate, redirect light emanating from the light source 18 to further direct or control the illumination.

In some embodiments, the light source 18 includes a plurality of LED lights arranged about the periphery of the distal end of the first housing element 30. The LED lights can produce white light or UV light to illuminate, for example, UV-luminescing dyes or materials. As shown in FIGS. 3, 5, 9, 10, 13 and 16, two LED lights are used. The two LED lights ensure that the lighting device 10 is capable of directing enough light toward a particular space to illuminate the area with a reasonable power consumption, while maintaining a streamline profile of the device 10 to ensure a user's view is not blocked, limiting weight and cost of the lighting device. However, as will be recognized by a person of ordinary skill in the art, any number of lights can be used depending on the need of the user, and any light source that is known or may become known can be used in place of the LED lights, such as photoluminescence, chemoluminescence, electroluminescence, snap sticks, and glow stick. Further, as seen in the figures, the lights 18 are substantially evenly angularly spaced in the device 10. This helps to more evenly distribute light. However, the invention contemplates any suitable arrangement of lights 18.

The device 10 can be removably attachable to a tool 12 or object using various attachment mechanisms. In the embodiment shown in FIGS. 8 and 11, the lighting device 10 can include a plurality of protrusions 40 that are arranged in recesses 42 formed in the housing 16 to removably attaching the lighting device 10 to a tool 14. The protrusions 40 are fixed within the recesses 42 by angled stops 43 that provide a frictional contact with the protrusions 40 by extending inwardly at an angle within the recesses 42 from the inner periphery of the housing 16. The protrusions 40 are also fixed within the recesses 42 by projections 44 that extend from the second housing element 32 and are contactable with the protrusions 40. In the shown embodiment, the protrusions 40 are oriented at a forward angle toward the distal end of the device 10. They can be spring-loaded. The protrusions 40 include a first limb 46, a second limb 48 extending from the first limb 46 at a forward angle, and a tang 50 extending from the second limb 48 at a lesser forward angle. The protrusion 40 and the tang 50 is arranged and configured to contact the outer surface of the tool 12 when the device 10 is installed onto the tool 12.

Figure 8:
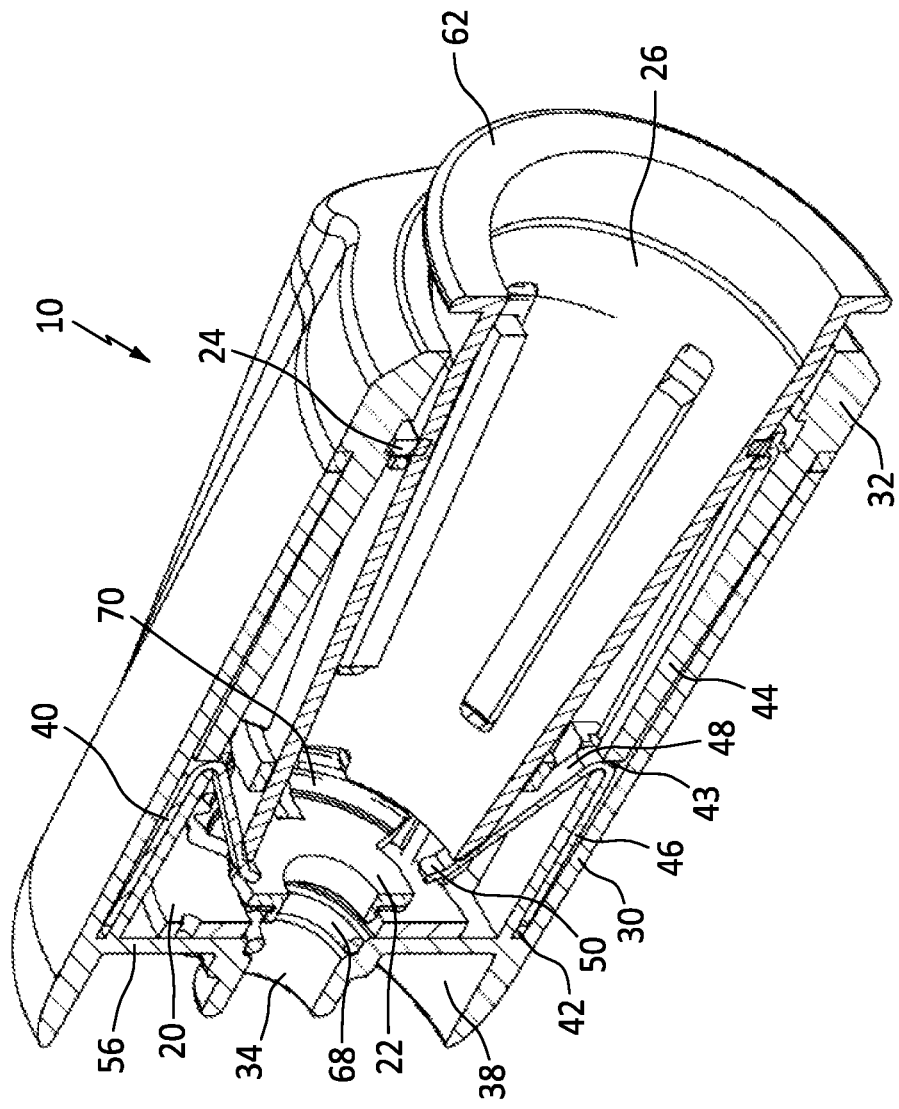
FIG. 8 is a rear perspective cross-sectional view of the lighting device of FIG. 1 taken along line A-A of FIG. 4.

The contact between the tangs 50 and the tool 12 maintains the device 10 positioned on the tool 12. Contact between a tang 50 and the outer surface of the tool 12 creates friction that helps prevent relative sliding movement between the device 10 and tool 12. The amount of friction depends in part on the force the tang 50 asserts against the tool 12. The force depends upon the degree of interference between the tool 12 and tang 50, and the spring characteristics of the protrusions 40. As to the former, the greater the interference, that is, the degree the outer surface of the tool 12 is larger than the space between the tangs 50 in their non-compressed state, the more the tool surface will compress the protrusions 40, e.g., outwardly in the embodiment seen in FIG. 8, and the greater the opposing spring force on the tool 12. With respect to the latter, the spring characteristics of the protrusion 40 depend upon the spring characteristics of the material out of which the protrusion 40 is made, and the configuration of the protrusion 40 itself. As seen in FIG. 8, the second limb 48 acts as a lever arm with respect to the first limb 46. The effective spring rate of the protrusion decreases with increasing length and forward angle of the second limb 48.

As should be appreciated by those of ordinary skill in the art, then, the amount of friction can be controlled, in part, by configuring the protrusion 40 and selecting the material of which the protrusion 40 is made. Accordingly, the frictional retaining force on the device 10 can be made sufficient to prevent the device 10 from unintended removal from the tool 12 under the expected operating conditions. The protrusion 40 can thus be manufactured out of metal, plastic, carbon fiber, or any other suitable material that is known or will become known.

The frictional force is also dependent, in part, upon the frictional coefficient of the material of the tang 50 that contacts the tool 12. For example, if a high frictional force is desired, the tang could be made of a relative high friction material, such as rubber or other elastomeric material, or include a sleeve, end cap, or coating on or over the contact surface of the tang to provide the desired friction and gripping force. For example, if the protrusion 40 is made from metal or plastic, this may impart strength and overall desired spring rates for the protrusion 40, but provides a low friction contact surface with the tool. The tang 50 may be coated or otherwise include a material, e.g., rubber, having a higher friction coefficient to provide the desired frictional characteristics.

Where the outer surface of the tool 12 is made of a relatively softer material, and the tang 50 is made of a sufficiently hard material or sharpened structure, e.g., has a sharp edge, the tang 50 may to a certain degree deform the outer surface of the tool 12, e.g., "dig into" it, so as to further secure the device 10 in addition to a merely frictional engagement. The inventor has found that even a small amount of deformation, in many cases not enough to adversely damage the tool 12, significantly increases the retention of the device 10.

In the embodiment shown, the forward angle of the second limb 48 provides self-locking or wedging effect against disengagement of the device 10 from the tool 12, while not overly inhibiting installation. As best seen in FIG. 8, when the device 10 is inserted onto the tool 12 (or, conversely, the tool 12 is inserted through the cavity/opening in the device 10), when the outer surface of the tool 12 contacts the tangs 50, it imparts a force on the tangs 50, and thus the protrusions 40, in a distal direction. This biases the protrusions 40 forwardly (distally) and outwardly, such that the retaining force on the tool 12 is moderated. On the other hand, when attempting to move the parts in the opposite direction (in FIG. 8, the tool 12 relatively to the right and the device 10 relatively to the left), contact between the tool 12 surface and the tang 50 imparts a proximal (rearward) force on the tangs 50 and thus the protrusions 40. This biases the protrusions backwardly (proximally) and inwardly, increasing the force of the protrusions 40 on the tool 12, e.g., wedging the protrusions 40 against the tool 12, and increasing the retention of the device 10 on the tool 50. This action assists in preventing unintentional disengagement of the tool 12 and device 10.

Figure 9:
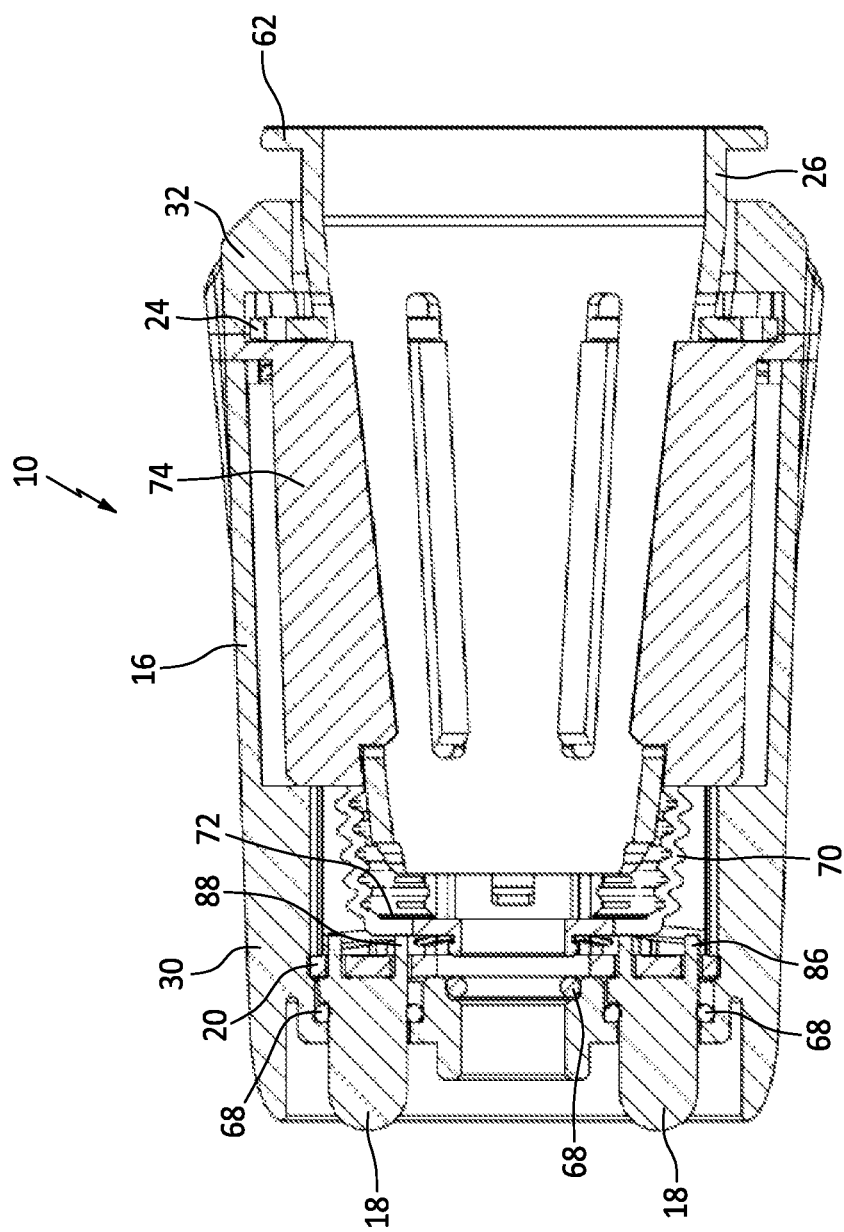
FIG. 9 is a cross-sectional view of the lighting device of FIG. 1 taken along line B-B of FIG. 6.

As seen in the illustrated embodiment, particularly in FIGS. 8 and 9, the sleeve 26 is received within the frame 22 and the frame 22 is received within the housing 16. The sleeve 26 includes a flange 62 extending outwardly at a proximal end and a chamfered distal end surface 64. The chamfered surface 64 abuts or is near the second limb 48 of the protrusion. To disengage the lighting device 10 from the tool 12, one applies a force to the flange 62 in the distal direction, which causes the sleeve 26 to flex or move axially toward the distal end of the light attachment 10. The chamfered surfaces 64 contact the second limb 48, and act as a wedge or ramp against the second limb 48. This imparts both a forward (distal) and radially outward force on the second limb 48, that deflects the second limb 48, e.g., out of engagement with the tool 12, and/or prevents the above-described wedging action on the protrusion 40 during removal. The device 10 can then be disengaged from the tool 12. In the illustrated embodiment, the sleeve 26 and flange 62 extend outwardly past (proximally) the housing 16, and forms the proximal end of the device 10. Thus, to disengage the device 10 from the tool 12, the user engages the rear (proximal) end of the device, e.g., the flange, and moves the device 10 distally (forwardly). Where the shaft 14 is too large for the device 10 to be removed with the shaft 14 in place in the tool 12, the shaft 14 is removed from the tool 12 so as to allow the device 10 to be removed.

In the illustrated embodiment, the sleeve 26 is tapered having a substantially conical or tapered shape to extend over the distal end of a tool 14 having a substantially conical or tapered shape. However, as will be recognized by a person of ordinary skill in the art, the sleeve 26 can take the form of any known shape to accommodate a shape of the tool 14 on which the sleeve 26 is to be arranged. For example, if the tool 14 is cylindrical or the device 10 is to be attached to the shaft 14 of the tool 12 that is cylindrical instead of a distal end of the tool 14, the sleeve 26 can be cylindrical to substantially match the contour of the tool 12 and/or shaft 14.

Those of ordinary skill in the art should recognize that although the illustrated embodiment utilizes angled spring-loaded protrusions 40, the protrusions 40 can take on a number of structural configurations while still ensuring a sufficient gripping force such that the attachment 10 will not become detected without manual force applied to the sleeve 26. For example, in some embodiments, the protrusions 40 are not spring-loaded but relatively rigid and plastically deformable. In such embodiments, the protrusions 40 may be plastically deformed when the device 10 is installed on the tool 12 and/or when the device 10 is removed from the tool 12. As a result, because a certain level of force on the protrusions 40 is required to deform them, the device 10 will not unintentionally disengage from the tool 12, but generally only when an intentional level of disengaging force is exerted on the device 10. In yet other embodiments, the protrusions 40 are breakable or separable from the housing 16 upon exertion of a certain level of disengagement force on the device 10 (and thus the protrusions 40). Once broken or separated, the protrusions 40 do not hold the device 10 on the tool 12. It should be understood by those of ordinary skill in the art that the protrusions 40 may be provided with a selected level of disengagement force, e.g., the force at which the protrusions 40 will sufficiently deform, break or separate to allow the device 10 to disengage from the tool 12. As one example, the protrusions 40 may include a weakened portion or area at which the protrusion 40 is designed to deform, break or separate at a determinable and/or selectable force.

Additionally, other attachment mechanisms and/or biasing members may be used in place of the protrusions 40. Examples include, but are not limited to, adhesives, latches, snaps or cinch ties or fasteners, crank fasteners, rings, eyelets or any other technology that is known or may become known. When the tool 12 contains material that is capable of being attracted to a magnetic material e.g., a ferrous material, the device 10 can in addition or alternatively include components that are magnetic. In this manner, the device 10 can be secured to the tool 12, at least in part, magnetically.

Figure 10:
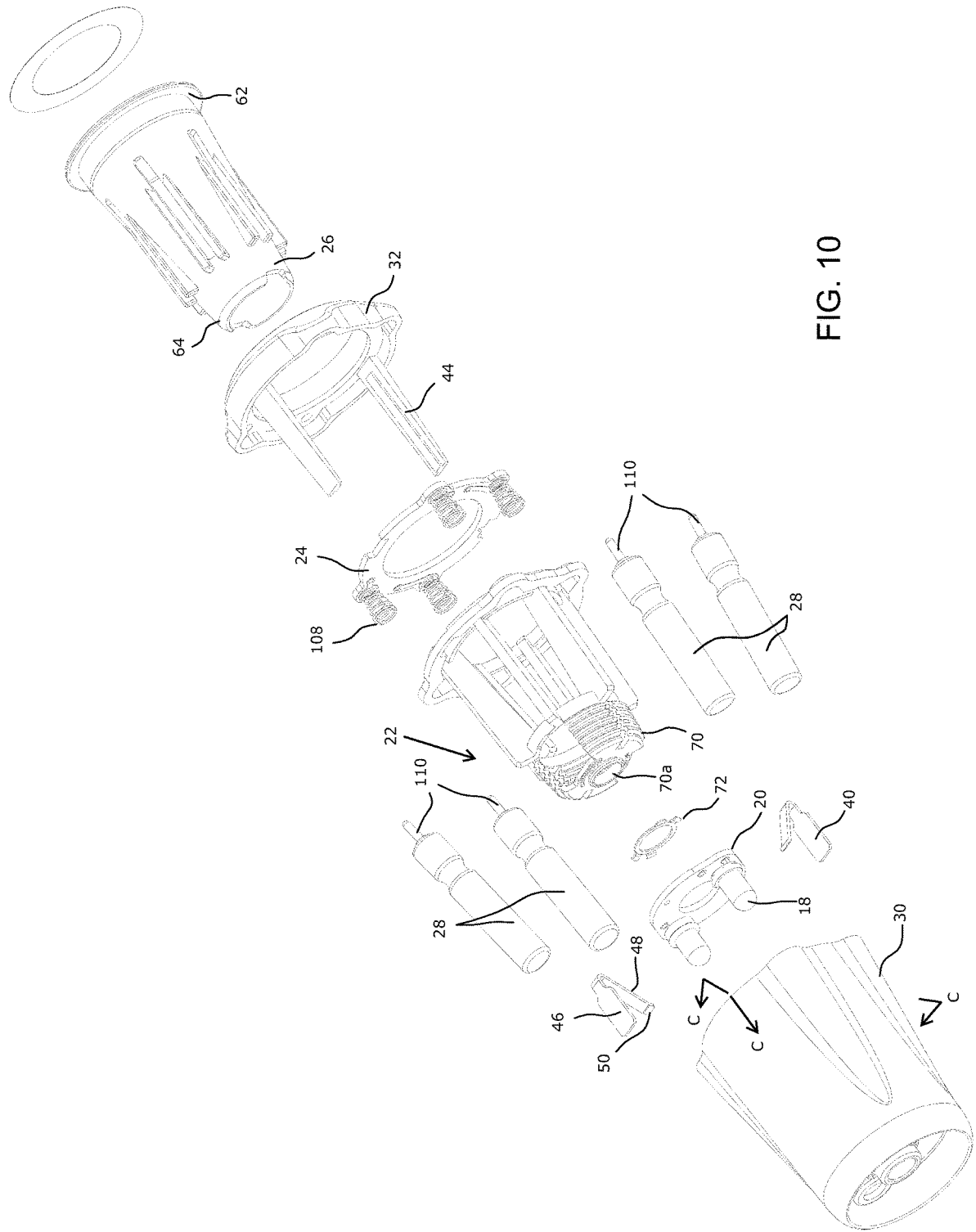
FIG. 10 is an exploded view of the lighting device of FIG. 1.

FIG. 10 is an exploded view of an embodiment of the lighting device 10 illustrating the components that comprise the lighting device 10 and their arrangement within the housing 16.

Figure 16:
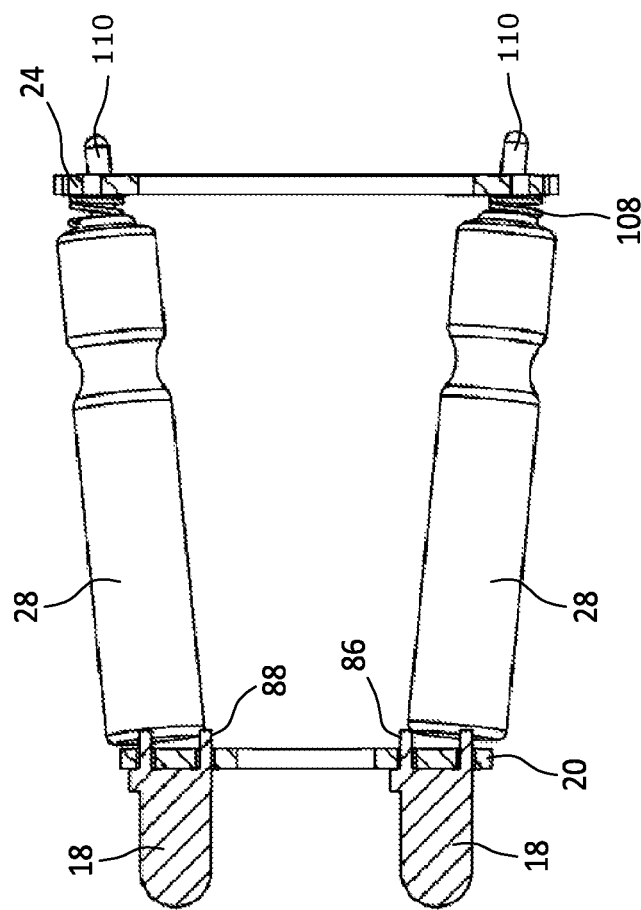
FIG. 16 is side view of the assembly of the first plate, the second plate and a power source disposed between the plates of the lighting device of FIG. 1.

As shown in FIGS. 10 and 16, the power source 28 can include a battery or batteries. The batteries 28 shown in FIGS. 10 and 16 are pin-type batteries, which allow for generally longitudinal orientation (proximal-distal) and a minimized radial profile (diameter) of the lighting device 10. However, any other type of power source, including solar power or capacitors, that is known or may become known can be used in place of batteries. Additionally, other types of batteries can be used in place of the pin-type batteries, such as, for example, strip-style batteries, coin batteries and cloth batteries. Further, the batteries can be for a single use or rechargeable. Single use or disposable batteries can include alkaline, carbon-zinc, lithium, silver-zinc, and zinc air. The pin-type battery 28 shown in FIGS. 10 and 16 is a single-use lithium battery. Such a pin-type battery produces a high density of energy (e.g., 800 Wh/l), can be used under a wide range of temperatures (e.g., −20° C. to approximately about 60° C.), can store energy for over two years, has a low discharge rate (e.g., less than 1%/year), is leak resistant, reliable, and is an eco-friendly product that is free of heavy metals.

Figure 11:
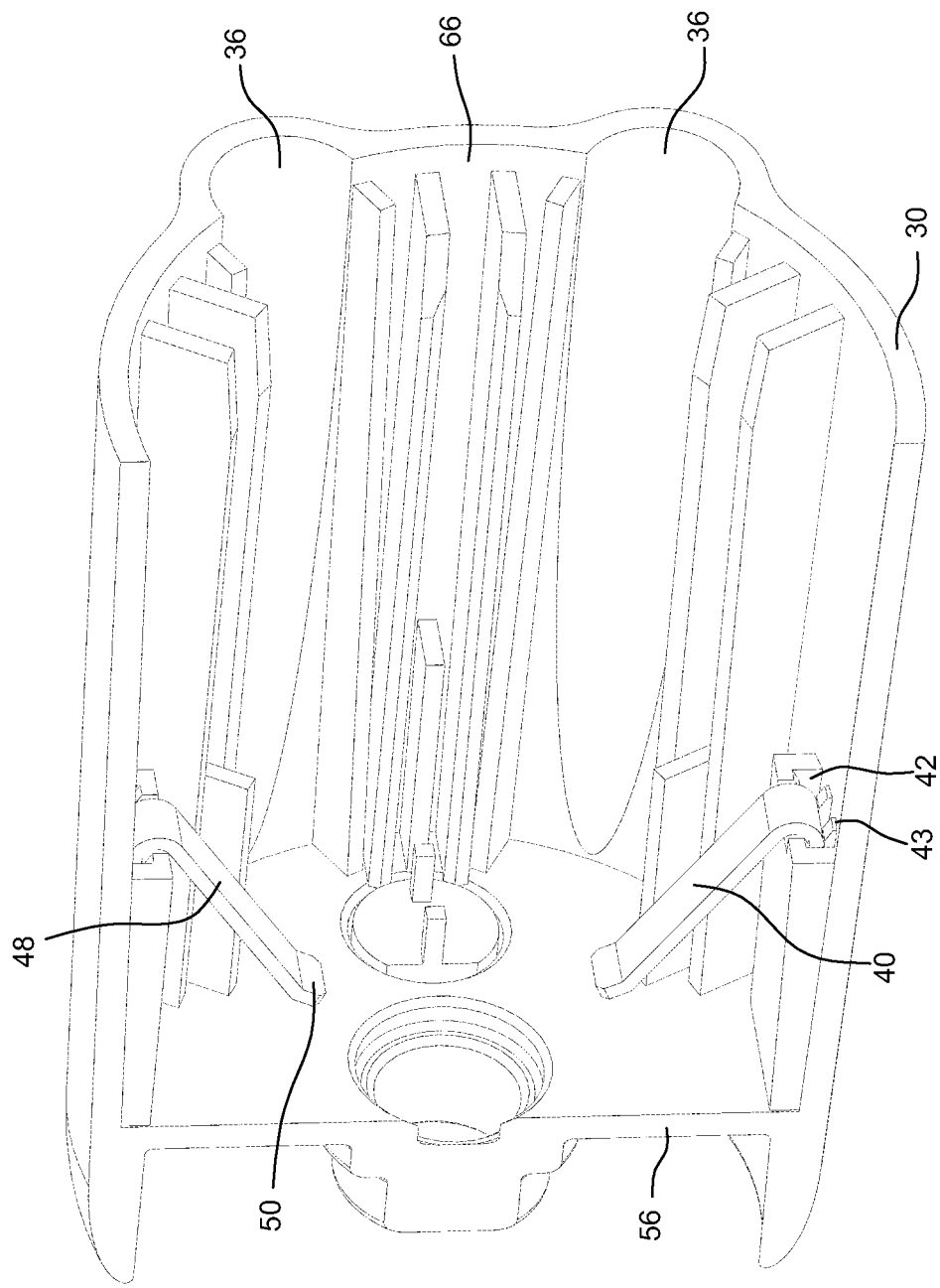
FIG. 11 is a rear perspective cross-sectional view of the outer housing of the lighting device of FIG. 1 taken along line C-C of FIG. 10.

FIG. 11 shows a cross-sectional view of an embodiment of the first housing element 30 taken along line C-C from FIG. 10. As discussed above, the first housing element 30 can include projections 36 that project outwardly therefrom to accommodate the profile of the batteries 28, recesses 42 formed within the first housing element 30 to receive the projections 40, and openings 34, 58, 60 formed in a wall 56 near the distal end of the housing 16. The first housing element 30 can further include a plurality of projections 66 extending inwardly to aid in connecting the housing 16 to the frame 22 and O-rings 68 or other elastomeric means can be arranged within the openings of the housing to protect against ingress of contaminants or fluids.

As seen best in FIGS. 9 and 10, the first plate 20 is arranged within the housing 16 between a wall 56 near the distal end of the housing 16 and the frame 22, and the light sources 18 project outwardly through openings 58, 60 in the wall 56 of the housing 16. The second plate 24 is arranged within the housing 16 near a proximal end of the housing 16.

Figure 13:
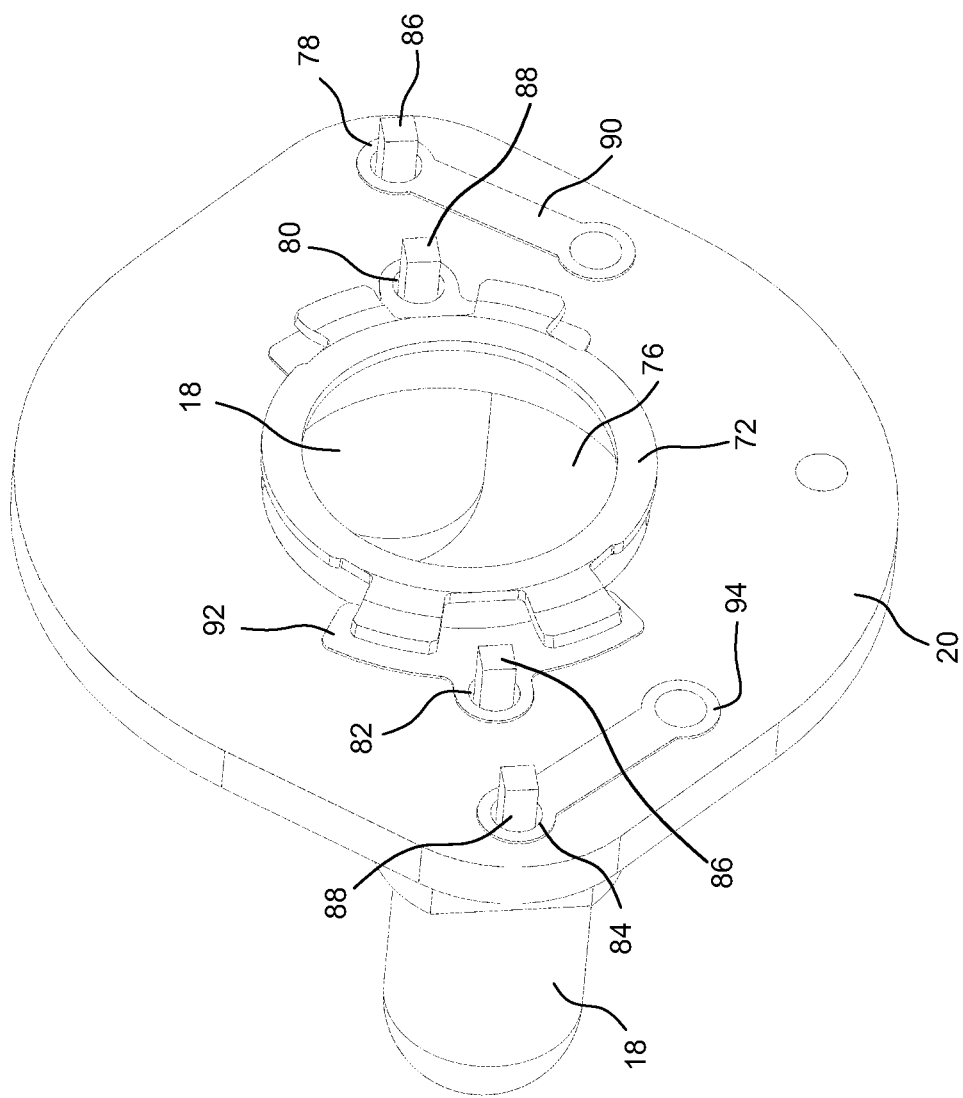
FIG. 13 is a rear perspective view of the first plate of the lighting device of FIG. 1 with the light source arranged thereon.

FIG. 13 shows an embodiment of the first plate 20 having an opening 76 therein for receiving therethrough a shaft 14 of a tool 12 and light sources 18 extending through a plurality of openings 78, 80, 82, 84 extending through the plate 20 about the periphery of the plate 20. The light source 18 include prongs 86, 88 that extend through openings 78, 80, 82, 84 in the first plate 20 and are contactable with the plurality of electric circuits 90, 92, 94 that are affixed to the first plate 20 or formed therein.

Figure 14:
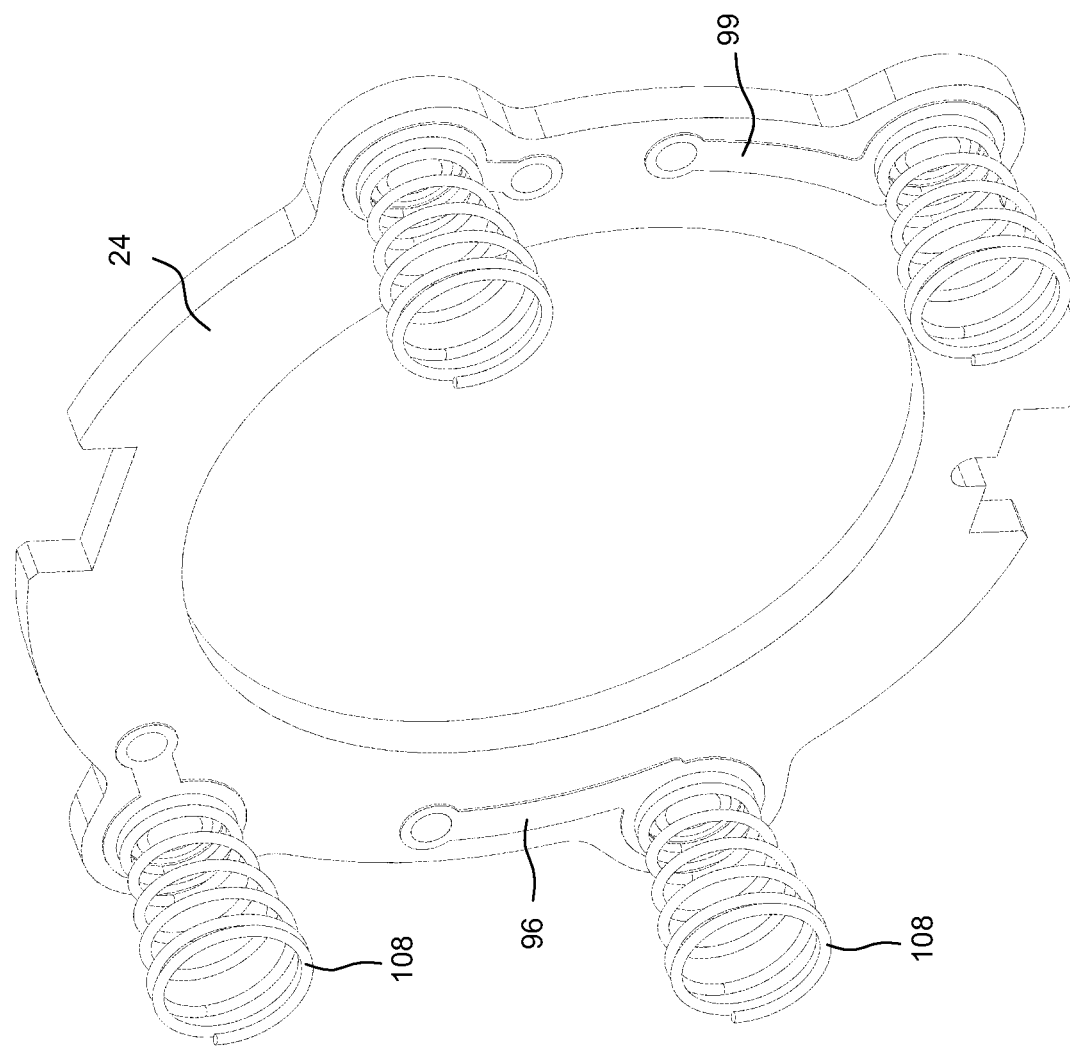
FIG. 14 is a front perspective view of the second plate of the lighting device of FIG. 1.
Figure 15:
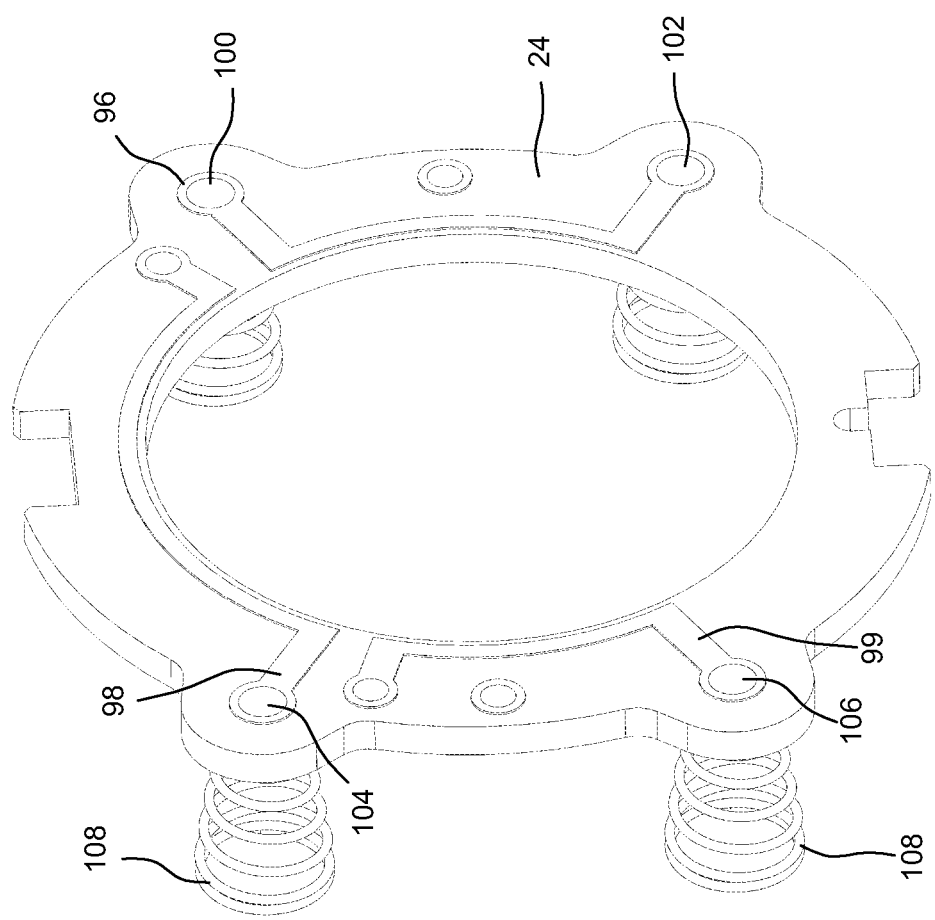
FIG. 15 is a rear perspective view of the second plate of the lighting device of FIG. 14.

FIGS. 14 and 15 show, respectively, front and rear perspective views of the second plate 24. The second plate 24 includes a plurality of electric circuits 96, 98, 99 that are affixed to the first plate 24 or formed therein, a plurality of openings 100, 102, 104, 106 extending through the circuits 96, 98 and second plate 24, a plurality of compression springs 108 affixed to the circuits 96, 98, 99 on a first side of the second plate 24 at the openings 100, 102, 104, 106 extending through the plate 24. Although compression springs 108 are shown in the embodiment, other biasing mechanisms that are known or may become known can alternatively be used.

As can be seen well in FIG. 16, a plurality of power sources 28 extend between the first plate 20 and the second plate 26 and the terminals 110 of the power source 28 extend through the openings 100, 102, 104, 106 in the second plate 26. After assembly, the terminals 110 can be soldered to the second side of the second plate 26 to fix the power sources 28 in place. The compression springs 108 form a contact with the conductive outer shell of the power source 28, which can be, for example aluminum or steel, in a compressed state. The restorative spring force in the compressing springs 108 help maintain contact with the shell of the power source 28. As can also be seen in FIG. 16, the radially-inward terminals 86, 88 of the light sources 18 are not in electrical communication with each other. Thus, no complete or closed circuit is formed, and no power flows to the light sources 18.

Figure 12:
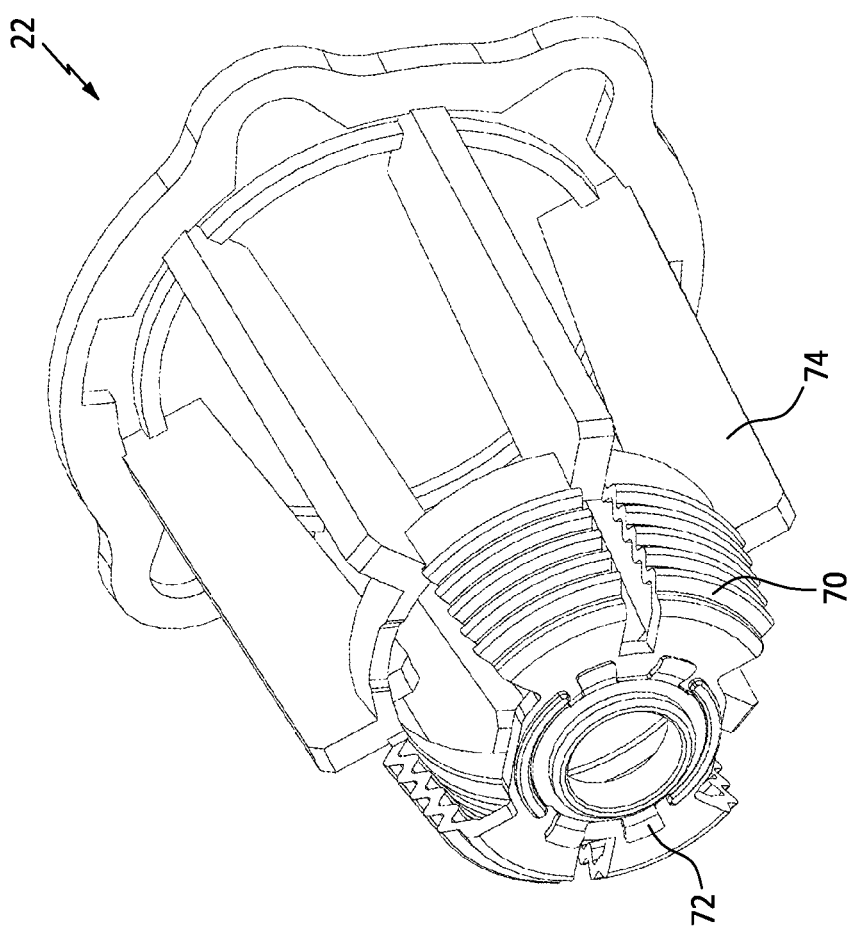
FIG. 12 is a front perspective view of the inner frame that is received within the outer housing of the lighting device of FIG. 1.

FIG. 12 is a perspective view of an embodiment of the frame 22. The frame 22 includes a plurality of bellows 70 that extend from a distal end of the frame 22, and a conductive ring or plate 72 made of any suitable conductive material, e.g., conductive metal, is affixed to the distal end of the frame 22 or molded therein. At least the bellows 70 of the frame 22 are made from an elastomeric material allowing the frame 22 and/or bellows 70 to expand (lengthen) and contract (shorten). Although the frame 22 is made at least in part from an elastomeric material, the frame 22 can be made from any other material that allows at least the bellows 70 to expand and contract. The frame 22 can thus be made from a combination of materials or a single elastomeric material.

Gaps extend about the circumference of the distal end of the frame 22, between the bellows 70 for clearance purposes and interaction with other elements of the device 10. The frame 22 also includes a plurality of projections 74 that extend radially inwardly and outwardly to connect the frame 22 to the housing 16 and the sleeve 26 to connect the frame 22 to other elements of the light attachment 10. Further, although the frame 22 and the sleeve 26 are shown in FIG. 10 as two independent elements, the frame 22 and the sleeve 26 can be formed as a single unitary element.

In an initial state prior to installation of the device 10 on the tool 12, as best seen in FIG. 9, the bellows 70 are in a natural condition sufficiently compressed so that conductive ring 72 is not in contact with, e.g., gapped from, the first plate 20. Because the radially-inward terminals 86, 88 of the light sources 18 are not in electrical communication with each other, the electrical circuit (as seen in FIG. 16) is open and the light sources are not illuminated. The bellows 70 have a bellows ring 70a (as seen, e.g., in FIG. 10) defining an opening through which the tool 12 extends upon installation of the device 10 on the tool 12.

During the assembly of the light attachment 10 on the tool 12, the bellows 70 are expanded axially. Once the device 10 is placed over a selected portion of the distal end of the tool 12, it engages the tool 12. During engagement, friction between the tool 12 and the frame 22, e.g., the bellows ring 70a causes the distal end of the frame 22, e.g., the bellows 70, to expand, i.e., lengthen, relative to the other components of the device 10. In particular, the conductive ring 72 moves distally relative to the first plate 20 until it contacts the first plate 20. More specifically, the conductive ring contacts the radially-inward prongs 86, 88 of the light sources 18, placing them in electrical communication with each other. This completes and closes the electrical circuit with the power source 28, electricity is delivered the light sources 18, and the light sources 18 illuminate.

During removal of the device 10 from the tool 12, a reverse action turns the light source 18 off. During removal, the frictional forces on the frame 22 and bellows 70 is in the opposite direction than during installation. These forces, and also the restorative spring force stored in the bellows 70 due to their extension during installation, cause the frame 22, e.g., the bellows 70, to contract, which moves the conductive plate 72 in a direction proximally relative to other components of the device 10. The conductive plate 72 thus separates from the first plate 20, and the radially-inward prongs 86, 88, as the bellows 70 contract or compress toward the position shown in FIG. 9. The prong 86, 88 are removed from electrical communication with each other, which opens the circuit. Thus, the light source 18 is no longer illuminated when the lighting device 10 is not attached to the tool 14.

It should be noted that the above configuration is but one way the light source 18 can be turned on and/or off. The invention contemplates any suitable way to accomplish this, either currently known or later discovered. By way of example only, the lighting device 10 can include a switch or button that the user manually operates to turn the device 10 on and off.

Figure 17:
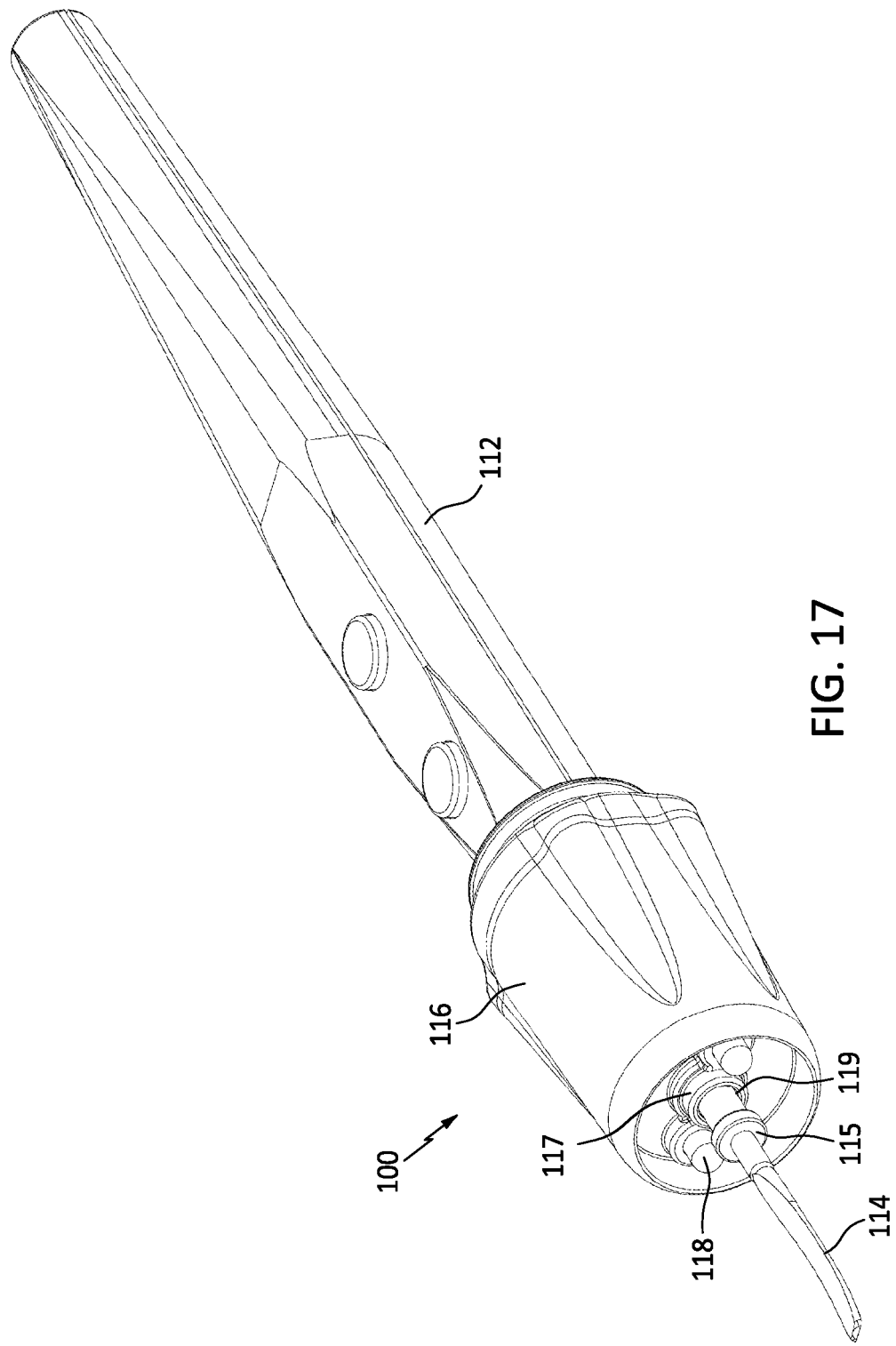
FIG. 17 is a front perspective view of another embodiment of a lighting device that is secured to the tool by a shoulder extending about the periphery of a shaft of a tool.

The embodiment shown in FIG. 17 shows an alternative cordless lighted device 100 that is retained on the tool 112 by the tool itself. The tool 112 has a proximal end and a distal end. The tool 112 has an opening at the distal end to receive the shaft 114, e.g., a blade. The shaft 114 is insertable into and retained by the body of the tool 112 in a known manner. In this example, the shaft 114 has collar, rim or shoulder 115 configured to seat against the distal end of the tool 112 when inserted.

The features of the lighted tool 100 are substantially the same as those of lighting device 10 except where indicated. For example, the device 100, similar to the lighted device 10, has a housing 116, and at least one light source 118 powered by a cordless power source, and receives the tool through an opening or cavity extending from the proximal end to the distal end of the device 100. The cavity is shaped and configured so that the device 110 encompasses, e.g., is attachable to, a predetermined portion of the tool 112. As illustrated, the device 110 is configured to engage upon the distal end of the tool 112. In this manner, the light source 118 is located as close to the shaft 114 as possible, e.g., close to the operating site, without interfering with the functioning of the tool 112.

As can be seen in FIG. 17, the housing 116 includes a protrusion 117 extending from the distal end and around the through opening in the device. The protrusion 117 forms a rim 119 at its distal end. The inner diameter of the protrusion 117 and the rim 119 is large enough to permit the shaft 114 to be inserted into and mounted to the distal end of the tool, but smaller than the outer diameter of the collar 115 of the shaft. Accordingly, after the shaft 114 is inserted into the tool, the dimensional interference between the collar 115 and the rim 119 prevents the device 100 from being removed off from the distal end of the tool 112. The shaft 114, and more specifically the shoulder 115, secures the device 110 to the tool. Where the shaft 144 can be removed from the tool 112, the device 110 can then be removed from the tool in a similar manner as described above with respect to the lighting device 10.

Figure 18:
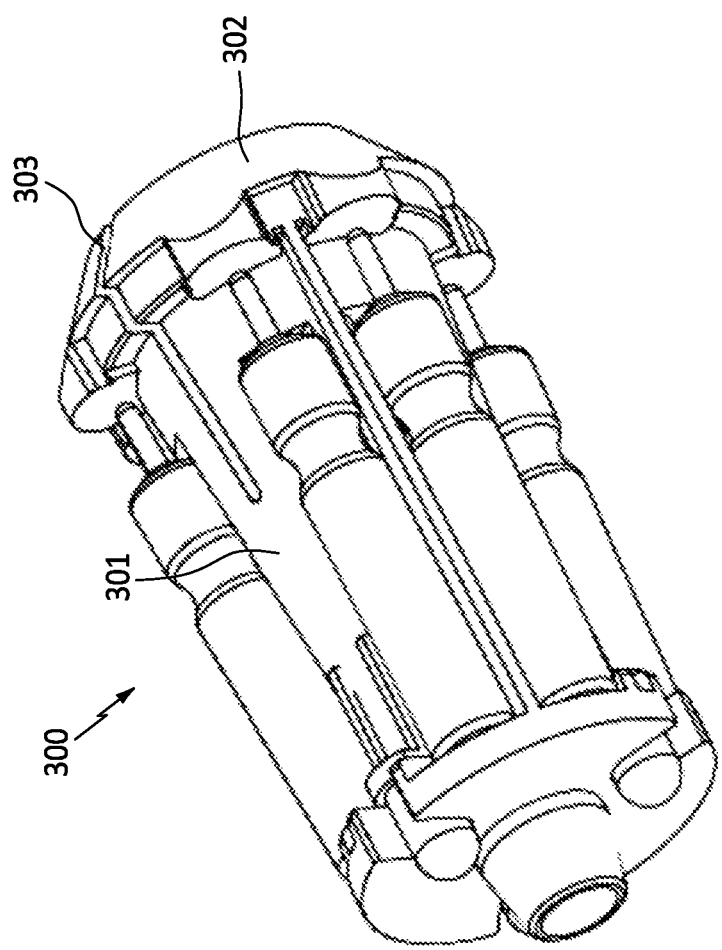
FIG. 18 is a perspective view of feature of yet another embodiment of a lighting device that includes a split collar.

An alternative embodiment shown in FIG. 18 shows an alternate manner of retaining a lighting device 300 on a tool. The features of the lighting device 300 are substantially the same as those shown in the embodiments of the lighting devices 10 and 100 except where indicated. The device 300 includes a housing 301 that includes split collar 302 with a slit 303 extending longitudinally partway through extending from the proximal end of the device 300 part way toward the distal end of the device 300. In this embodiment, the housing 301 is made of an at least slightly flexible or spring-like material. The cavity or opening of the device 300 is smaller than the outer surface of the tool. When the device 300 is installed on the tool, the dimensional interference between the tool and the cavity of the device 300 causes the slit to spread or expand due to the flexibility of the material of the housing 301. Thus, the cavity or opening will expand to accommodate the outer surface of the tool.

At the same time, the restorative spring-like force stored in the deflected material of the housing 301 will impose an opposing compressive force against the outer surface of the tool, providing a gripping and/or frictional force on the tool. This force will help maintain the device 300 attached to the tool. As those of ordinary skill in the art should appreciate, the retention force can be selected as desired or suitable. For example, the force can be selected by selecting, among other things as will be understood by those of ordinary skill in the art, the material of the housing in order to have a selected material flexibility, the amount of dimensional interference between the tool and the cavity of the device 300, which determines the amount of flexing or deflection necessary to install the device 300 on the tool, and the shape, size and configuration of the slot 301, which effects the overall flexibility of the housing 301.

Figure 19:
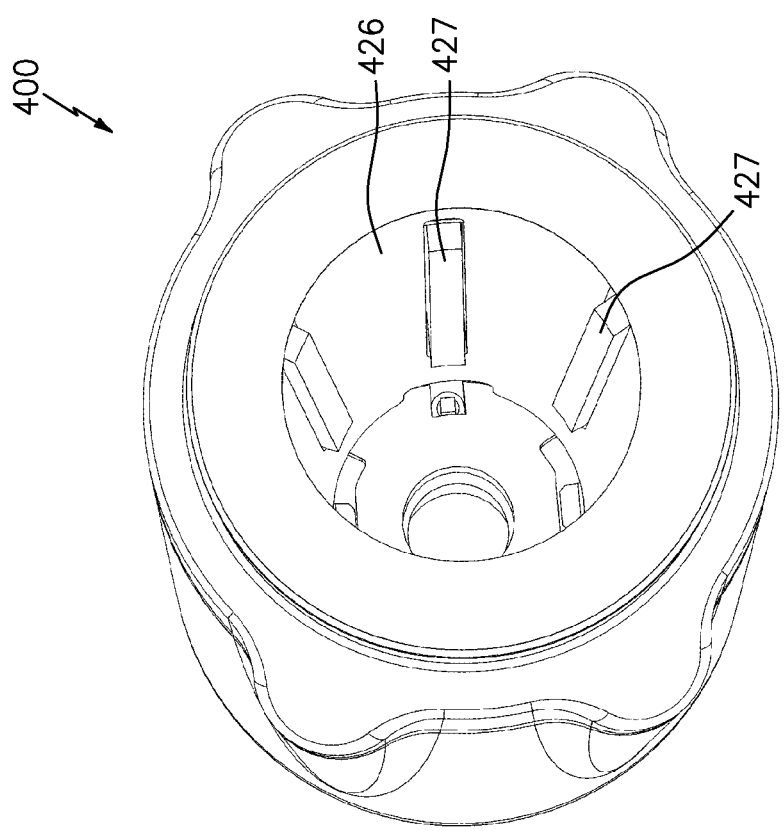
FIG. 19 is a perspective view of another embodiment of a lighting device that includes projections extending inwardly from a sleeve to removably secure the device to a tool.

Another embodiment shown in FIG. 19 depicts a further alternative configuration for securing a lighting device 400 to a tool. The features of the lighting device 400 are substantially the same as those shown in the embodiments of the lighting devices 10, 100 and 300 except where indicated. In this embodiment, the sleeve 426 includes a plurality of projections 427 extending from the inner peripheral surface of the sleeve 426 radially inwardly into the cavity of the device into which the tool is received. The projections 427 are flexible, compressible and/or elastomeric. The distance the projections 427 extend into the cavity is selected to provide a dimensional interference between the projections 427 and the outer surface of the tool. When the tool is inserted into the cavity, the projections are flexed or compressed to accommodate the tool. In turn, the restorative spring force in the compressed/flexed projections 427 asserts an opposing inwardly directed compressive force against the outer surface of the tool. This generates a gripping/frictional force between the projections 427 and the tool that helps maintain the device 400 engaged on the tool. Those of ordinary skill in the art should recognize that the retention force can be selected as desired or suitable. For example, the force can be selected by selecting, among other things as will be understood by those of ordinary skill in the art, the material of the projections 427 in order to have a selected material compressibility/flexibility and also frictional coefficient between the projections 427 and tool, and the amount of dimensional interference between the tool and the projections 427, which determines the amount of flexing or deflection necessary to install the device 400 on the tool, and thus the opposing compressive force. As will be appreciated, the retention force can be selected so as that the lighting device 400 will not become unintentionally disengaged from the tool during operation, but provides a reasonable level of force for the user to install and disengage the lighting device 400.

In other embodiments, the projections 427 contain magnetic material. In such embodiments, the device 400 may be secured to a magnetic tool 12, at least in part, magnetically. As those of ordinary skill in the art will understand, the degree of magnetic force between the projections 427 and the tool 12 may be selected to be great enough so as to substantially prevent unintentional disengagement between the device 400 and the tool 12, but at a level that permits intentional disengagement when desired.

The lighting devices of the invention provide multiple advantages. One advantage of the light attachment is its size. The light attachment has a diameter that extends only somewhat beyond the outer periphery of the tool to allow a user to easily manipulate the tool while not hindering maneuverability or blocking the user's line of vision. The packaging advantage is due, in certain embodiments, to the use of pin-shaped batteries oriented in a generally proximal-distal alignment with the device.

Another advantage is that the light attachment is easily attachable to a tool and detachable from the tool. As discussed above, the light attachment can easily slide over a distal end of a tool for engagement with the tool during use. When a user wants to remove the light attachment from the tool, the user merely has to apply axial pressure to the proximal end of the light attachment to disengage the light attachment. At the same time, unintentional dislodging of the device from the tool is mitigated.

Yet another advantage is that the light attachment simultaneously attaches to a tool and illuminates a light source ensuring efficient assembly and use. The light attachment includes attachment means that are engageable and disengageable with a tool; there are no additional fasteners required to ensure the device will not automatically become disengaged from the tool during use.

In addition, the devices are cordless with a self-contained power source. The device does not require attachment via an electrical cord to a remote electrical outlet or light source. A cord adds unwieldiness to the tool, and may require assistance to manipulate. Known corded devices may also become hot and burn the user and/or the patient, and possibly even cause a fire. The present invention decreases the risk of burning or causing a fire.

A further advantage is that the light attachment of the invention is securable to the tool at a desired or selected location. This permits optimal placement of the device, both from an illumination perspective and an operational perspective of the tool.

As may be recognized by those of ordinary skill in the pertinent art based on the teachings herein, numerous changes and modifications may be made to the above-described and other embodiments of the present invention without departing from its scope as defined in the appended claims. Accordingly, it is to be understood that this detailed description is to be taken as illustrative and not to be limited to the specific embodiments disclosed and that modifications and other embodiments are intended to be included within the scope of the appended claims. Further, although specific, terms are employed herein, they are used in a generic and descriptive sense only and not for purposes of limitation.

What is claimed is:

1. A lighting device, comprising:
a housing having a proximal end and a distal end and defining an interior cavity extending from the proximal end to the distal end and forming an opening extending through the housing from the proximal end to the distal end configured to removably receive therein at least a portion of a tool;
at least one light source disposed substantially at the distal end of the housing that is adapted and configured to illuminate a field of view; and
at least one protrusion or projection extending into the interior cavity and configured to engage the at least a portion of the tool and removably secure the lighting device to the tool, and including a first portion configured to engage the tool and a second portion that spring-loads or provides a spring force on the first portion when the tool is located in the opening.

2. A lighting device according to claim 1, wherein the first portion defines a tang and/or the second portion defines a lever arm.

3. A lighting device as defined in claim 1, wherein the second portion is flexible, compressible and/or elastomeric.

4. A lighting device according to claim 1, wherein the at least one protrusion or projection extends into the interior cavity at an angle to the housing toward the distal end.

5. A lighting device according to claim 1, wherein the first portion is adapted to generate friction with the at least a portion of the tool.

6. A lighting device according to claim 1, wherein the first portion includes an elastomeric material.

7. A method comprising:
installing a lighting device onto a tool, the lighting device comprising:
a housing having a proximal end and a distal end and defining an interior cavity extending from the proximal end to the distal end and forming an opening extending through the housing from the proximal end to the distal end configured to removably receive therein at least a portion of the tool;
at least one light source disposed substantially at the distal end of the lighting device that is configured to illuminate a field of view; and
at least one protrusion or projection extending into the interior cavity and configured to engage the at least a portion of the tool and removably secure the lighting device to the tool;
wherein the at least one protrusion or projection (i) includes a lever arm extending into the interior cavity; (ii) includes a first portion configured to engage the tool and a second portion that spring-loads or provide a spring force on the first portion when the tool is located in the opening; and/or (iii) includes a tang configured to engage the at least a portion of the tool and removably secure the lighting device to the tool;
wherein the installing step includes:
moving the tool and the lighting device relative to each other and locating the at least a portion of the tool within the opening; and
engaging the at least a portion of the tool with the at least one protrusion or projection and, in turn, removably securing the lighting device to the tool with the at least one protrusion or projection.

8. A method according to claim 7, wherein the at least one protrusion or projection includes a first limb and a second limb extending at an angle from the first limb toward the distal end.

9. A method according to claim 7, wherein the at least one protrusion includes an elastomeric sleeve extending over or a coating applied to an end portion thereof adapted to generate friction with the at least a portion of the tool.

10. A method according to claim 7, further including:
engaging the at least one protrusion or projection so as to disengage the at least one protrusion or projection from the tool; and
removing the lighting device from the tool.

11. A method according to claim 10, wherein
the lighting device further includes a movable portion movable between a first position wherein the movable portion does not disengage the at least one protrusion or projection from the tool and a second position wherein the movable portion engages the at least one protrusion or projection and disengages at least one protrusion or projection from the tool; and
the step of engaging the at least one protrusion or projection includes moving the movable portion from the first position to the second position.

12. A method according to claim 7, wherein the tool is an electrosurgical instrument.

13. A lighting device comprising:
a housing having a proximal end and a distal end and defining an interior cavity or opening extending from the proximal end to the distal end configured to removably receive therein at least a portion of the tool;
at least one protrusion or projection extending into the interior cavity or opening adapted and configured to engage the at least a portion of the tool and removably secure the lighting device to the tool;
at least one light source disposed substantially at the distal end of the lighting device that is adapted and configured to illuminate a field of view; and
a movable portion movable between a first position wherein the movable portion does not disengage the at least one protrusion or projection from the tool and a second position, wherein upon movement of the movable portion from the first position to the second position, the at least one protrusion or projection moves in a direction away from the tool.

14. A lightning device according to claim 13, wherein the movable portion is engageable by a user.

15. A lighting device according to claim 13, wherein in the second position the movable portion is engaged with the at least one protrusion or projection.

16. A method comprising:
installing a lighting device onto a tool, the lighting device comprising:
a housing having a proximal end and a distal end and defining an interior cavity or opening extending from the proximal end to the distal end configured to removably receive therein at least a portion of the tool;
at least one protrusion or projection extending into the interior cavity or opening adapted and configured to engage the at least a portion of the tool and removably secure the lighting device to the tool;
at least one light source disposed substantially at the distal end of the lighting device that is adapted and configured to illuminate a field of view; and a movable portion movable between a first position wherein the movable portion does not disengage the at least one protrusion or projection from the tool and a second position, wherein upon movement of the movable portion from the first position to the second position, the at least one protrusion or projection moves in a direction away from the tool;

wherein the installing step includes:

moving the tool and the lighting device relative to each other and locating the at least a portion of the tool within the interior cavity or opening; and engaging the at least a portion of the tool with the at least one protrusion or projection and, in turn, removably securing the lighting device to the tool with the at least one protrusion or projection;

the method further including moving the movable portion from the first position to the second position, whereby the at least one protrusion or projection moves in a direction away from the tool; and removing the lighting device from the tool.

17. A method according to claim 16, wherein in the second position the movable portion is engaged with the at least one protrusion or projection.

18. A method according to claim 16, wherein the step of moving the movable portion includes moving the movable portion in a distal direction toward the distal end.

19. A method according to claim 16, wherein the movable portion is engageable by a user, and the step of moving the movable portion includes a user engaging the movable portion.

20. The method according to claim 16, wherein the tool is an electrosurgical handheld instrument, and the method includes, prior to the removing step, detaching an electrosurgical blade from the electrosurgical instrument.

21. The method according to claim 16, wherein the tool is an electrosurgical handheld instrument, and the method includes attaching an electrosurgical blade to the electrosurgical instrument prior to the installing step.

22. The method according to claim 16, wherein the tool is an electrosurgical handheld instrument, and the method includes attaching an electrosurgical blade to the electrosurgical instrument by inserting a proximal end of the electrosurgical blade through a distal end of the interior cavity or opening.

23. The method according to claim 16, wherein the tool is an electrosurgical handheld instrument, and the method includes detaching an electrosurgical blade from the electrosurgical instrument; and (a) re-attaching the electrosurgical blade to the electrosurgical instrument or (b) attaching a second electrosurgical blade to the electrosurgical instrument without removing the lighting device from the electrosurgical instrument.

* * * * *